(12) United States Patent
Thiemermann

(10) Patent No.: US 9,623,005 B2
(45) Date of Patent: Apr. 18, 2017

(54) ARTEMISININ AND ITS DERIVATIVES FOR USE IN THE TREATMENT OF TRAUMA HAEMORRHAGE AND ASSOCIATED CONDITIONS

(75) Inventor: Christoph Thiemermann, London (GB)

(73) Assignee: Queen Mary University of London, London (GB)

( * ) Notice: Subject to any disclaimer, the term of this patent is extended or adjusted under 35 U.S.C. 154(b) by 357 days.

(21) Appl. No.: 14/125,032

(22) PCT Filed: Jun. 8, 2012

(86) PCT No.: PCT/EP2012/060929
§ 371 (c)(1),
(2), (4) Date: May 11, 2015

(87) PCT Pub. No.: WO2012/168450
PCT Pub. Date: Dec. 13, 2012

(65) Prior Publication Data
US 2015/0297558 A1    Oct. 22, 2015

(30) Foreign Application Priority Data

Jun. 10, 2011 (GB) .................................. 1109845.6
Jun. 10, 2011 (GB) .................................. 1109846.4
Jun. 10, 2011 (GB) .................................. 1109847.2

(51) Int. Cl.
*A61K 31/357* (2006.01)
*C07D 493/18* (2006.01)
*A61K 31/52* (2006.01)
*A61K 45/06* (2006.01)

(52) U.S. Cl.
CPC ............ *A61K 31/357* (2013.01); *A61K 31/52* (2013.01); *A61K 45/06* (2013.01); *C07D 493/18* (2013.01)

(58) Field of Classification Search
CPC ........................... A61K 31/357; C07D 493/18
See application file for complete search history.

(56) References Cited

U.S. PATENT DOCUMENTS

| | | | |
|---|---|---|---|
| 2008/0139641 A1 | 6/2008 | Meyer | |
| 2008/0139642 A1 | 6/2008 | Li et al. | |
| 2010/0137246 A1 | 6/2010 | Hyde et al. | |
| 2011/0077258 A1 | 3/2011 | Carvalho et al. | |

FOREIGN PATENT DOCUMENTS

| | | |
|---|---|---|
| CN | 102552908 A | 7/2012 |
| WO | 00/04026 | 1/2000 |
| WO | 2004028476 A2 | 4/2004 |
| WO | 2007/125397 | 11/2007 |
| WO | 2008/005276 | 1/2008 |
| WO | 2008/005376 | 1/2008 |
| WO | 2010/110747 | 9/2010 |
| WO | 2010132821 A2 | 11/2010 |
| WO | 2010135427 A2 | 11/2010 |
| WO | 2012033266 A1 | 3/2012 |
| WO | 2012168450 A1 | 12/2012 |

OTHER PUBLICATIONS

Kozikowski et al (2011): STN International, HCAPLUS database (Columbus, Ohio), Accession No. 2011: 108897.*
Mootha et al (2010): STN International, HCAPLUS database (Columbus, Ohio), Accession No. 2010: 1433046.*
Thiele et al (2009): STN International, HCAPLUS database (Columbus, Ohio), Accession No. 2009: 1437447.*
Sun et al., "Effect of artemisinin on ischemia/reperfusion injury of isolated rat myocardium", Zhonggou Zhongyao Zazhishe, 2008, 32(15):1547-51.
Wang et al., "Effect of artesunate on endotoxin-induced uveitis in rats", Invest Ophthlmol Vis Sci, 2011, 52(2):916-9.
Li et al., "Antimalarial artesunate protects sepsis model mice against heat-killed *Escherichia coli* challenge by decreasing TLR4, TLR9 mRNA expressions and transcription factor NF-kappa B activation", Int Immunopharmacol, 2008, 8(3):379-89.
Anyasor et al., Evaluation of selected biochemical parameters in renal and hepatic functions following oral administration of artesunate to albino rats, Resaercher 2011 3(7):30-34.
Bellomo et al., Acute kidney injury, Lancet 2012 380:756-66.
Bellomo et al., Acute renal failure—definition, outcome measures, animal models, fluid therapy and information technology needs: the second international consensus conference of the acute dialysis quality initiative (ADQI) group, Critical Care 2004 8:R204-12.
Campos et al., Effects of sodium artesunate, a new antimalarial drug, on renal function, Kidney Int. 2001 59(3):1044-51.
Halloran, Immunosuppressive drugs for kidney transplantation, N Eng J Med 2004 351:2715-29.
International Search Report and Written Opinion dated Mar. 1, 2013 for International Application No. PCT/EP2012/075306.
Johnson et al., The delayed administration of IKK-16, a specific iKKbeta inhibitor, attenuates acute kidney injury in rat recovery model of unilateral renal ischaemia, BPS Winter Meeting London 2012.
Mirshafiey et al., Therapeutic effect of artemether in an experimental model of nephrosis, Pharmaceutical Biology 2008 46(9):639-46.
Nankivell et al., Rejection of the kidney allograft, N Eng J Med 2010 363:1451-62.
Wu et al., Effect of artemisinin combined with glucocorticoid on the expressions of glucocorticoid receptor alpha mRNA, glucocorticoid receptor beta mRNA and P300/CBP protein in lupas nephritis mice, Chin J Integr Med 2011 17(4):277-82.

(Continued)

Primary Examiner — Golam M M Shameem
(74) Attorney, Agent, or Firm — Stradley Ronon Stevens & Young, LLP

(57) ABSTRACT

The present invention relates to the treatment of trauma haemorrhage or trauma haemorrhage-induced organ injury and associated disorders (in particular stoke, burns and brain injury) using the anti-malarial compound artemisinin and its derivatives. The present invention also relates to the treatment of myocardial infarction and coronary heart disease (and associated disorders) using the anti-malarial compound artemisinin and its derivatives. The present invention also relates to the use of artemisinin and its derivatives in coronary artery bypass surgery, heart transplantation, and diseases associated with ischaemia-reperfusion.

12 Claims, 8 Drawing Sheets

(56) References Cited

OTHER PUBLICATIONS

Wu et al., Therapeutic effect of artemisinin on lupus nephritis mice and its mechanisms, Acta Biochem Bioshys Sin 2010 42:916-23.
Golenser et al., Current perspectives on the mechanism of action of artemisinins, International Journal Parasitology 2006 36:1427-1441.
Gohil et al., Nutrient-sensitized screening for drugs that shift energy metabolism from mitochondrial respiration to glycolysis, Nature Biotech 2010 28(3):249.
Aldieri et al., Artemisinin inhibits inducible nitric oxide synthase and nuclear factor NF-kB activation, FEBS Letters 2003 552:141-144.
Hierholzer et al., Essential role of induced nitric oxide in the initiation of the inflammatory response after hemorrhagic shock, J Exp Med 1998 187(6):917-928.
Yasuhara and Date, Regenerative medicine for traumatic brain injury, Japan J Neurosurg 2010 19:210-215.
Wu et al., Establishment of mice nephritis models and observation of effects of dihydroartemisinin on release of inflammatory cytokines, Huaxi Yizue 2011 26(7):1028-1031.
Non-Final Office Action dated Mar. 30, 2016 in U.S. Appl. No. 14/651,298.
Shock: Shock and Fluid Resuscitation: Merck Manual 18th Edition Japanese Version; retreived from the internet, Jul. 14, 2016, http://merckmanualjp/mmpej/sec06/ch067/ch067b.html.
Respiratory arest: respiratory arrest and cardiac arrest: Merck Manual 18th Edition Japanese version; Jul. 14, 2016; retreived from the Internet http://marckmanual.jp/mmpej/sec06/ch064/ch06413.html.
Emergency Medical Service for the treatment of gross hematuria, Treatment Plan Today (Japan) 2002.
Final Office Action dated Sep. 8, 2016 in U.S. Appl. No. 14/651,298.
Mishra et al., Acute renal failure in falciparum malaria, JIACM 2002 3(2):141-147.
Annual Meeting Abstracts of the Pharmaceutical Society of Japan, 2001, vol. 121(1), p. 204.
Lee et al., Effect of Adenosine Triphosphate in Renal Ischemic Injury: Involvement of NF-kB, Journal of Cellular Physiology 2005 204:792-799.
Li et al., Dehydroarteannuin ameliorates lupus syndrome of BXSB mice by inhibiting production of TNF-alpha and blocking the signalling pathway NK-kappa B translocation, International Immunopharmacology 2006 6:1243-1250.
Mishra et al., Malaria and Acute Kidney Injury, Seminars in Nephrology 2008 28(4):395-408.
Razavi et al., Treatment of Experimental Nephrotic Syndrome with Artesunate, International Journal of Toxicology 2007 26:373-380.
Thanaketpaisam et al., Artesunate enhances TRAIL-induced apoptosis in human cervical carcinoma cells through inhibition of the NF-kB and PI3K/Akt signalling pathways, International Journal of Oncology 2011 39:279-285.
Notice of Allowance dated Nov. 11, 2016 from U.S. Appl. No. 14/651,298, filed Jun. 11, 2015.
Pasqual, M. et al., "Strategies to improve long-term outcomes after renal transplantation", N Engl J Med, 2002 346(8):580-90.

* cited by examiner

ARTEMISININ AND ITS DERIVATIVES FOR USE IN THE TREATMENT OF TRAUMA HAEMORRHAGE AND ASSOCIATED CONDITIONS

The present invention relates to the treatment of trauma haemorrhage or trauma haemorrhage-induced organ injury and associated disorders (in particular stoke, burns and brain injury) using the anti-malarial compound artemisinin and its derivatives. The present invention also relates to the treatment of myocardial infarction and coronary heart disease (and associated disorders) using the anti-malarial compound artemisinin and its derivatives. The present invention also relates to the use of artemisinin and its derivatives in coronary artery bypass surgery, heart transplantation, and diseases associated with ischaemia-reperfusion.

Trauma haemorrhage occurs when patients lose a considerable amount of their blood volume, for example due to internal bleeding or other injury. The resulting decrease in perfusion (the process of blood entering the tissues) of organs is insufficient to meet the metabolic needs of the cells. The reduced flow places significant strain on the organs of the patient and can lead to hypoxemia (a lack of oxygen in arterial blood), multiple organ failure and eventually cardiac arrest and death.

Current treatments for trauma haemorrhage are based on replacing the lost blood volume using intravenous fluids and blood transfusions to establish reperfusion of the organs. However, the damage caused to organs may have already occurred by the time the blood transfusion is available, in particular trauma haemorrhage-induced organ injury or multiple organ failure. Trauma haemorrhage is a significant problem and has numerous causes, including as a post-surgery complication. It can go undetected if it is a result of sustained internal bleeding.

Early identification and treatment is therefore essential to patient survival and recovery and there remains in the art a need for effective treatments to minimise the damage caused as a result of haemorrhagic shock.

Myocardial infarction (MI, also known as a heart attack) is an interruption of the blood supply to part of the heart. The interruption in blood supply is usually due to an occlusion of the vessel by a blood clot following the rupture of an atherosclerotic plaque, or even as a result of vessel spasm that cuts off the blood flow through the vessel, or infection. The resulting ischaemia can cause damage or death of the affected myocardium. The damaged heart tissue conducts electrical impulses more slowly that normal heart tissue and therefore disrupts the normal rhythm of the heart.

There are several risk factors for myocardial infarction and atherosclerosis, including diabetes, obesity, smoking, high blood pressure, stress, excessive alcohol consumption and old age. Coronary heart disease (a progressive failure of the coronary circulation to supply adequate circulation to cardiac muscle) often precedes MI and is treated with a combination of approaches, including lifestyle changes (smoking cessation, exercise, weight loss) as well as pharmacological interventions (for example the cholesterol lowering drugs statins, angiotensin converting enzyme (ACE) inhibitors and calcium channel blockers) and surgical interventions (for example angioplasty, stents, coronary artery bypasses and heart transplants) to reduce the risk of a potentially fatal MI. MI is a medical emergency and requires immediate medical attention to limit the damage to the myocardium and to prevent further complications. Severe MIs or can lead to cardiac arrest and death, and the World Health Organisation estimated that 12.6 percent of worldwide deaths in 2002 were from ischaemic heart disease.

Artesunate is an anti-malarial drug and is a derivative of artemisinin (also known as qinghaosu), a compound originally isolated from the Chinese herb *Artemisia annua* L. This family of compounds are sesquiterpene lactones, and although artesunate is known to result in adverse side effects (such as bradycardia, electrogram abnormalities, gastrointestinal disturbances and fever), its use in combination with other pharmacologically active agents for the treatment of *falciparum* malaria is standard.

US 2011/0077258 describes the treatment of malaria using artemisinin derivatives in combination with an adjuvant that promotes vasodilation. US 2008/0139642 describes artemisinin derivatives and their preparation and use in immunosuppression. WO 2010/110747 describes the use of artemisinin derivates for the treatment of asthma and chronic obstructive pulmonary disease (COPD). US 2010/0137246 relates to anti-inflammatory compositions that modulate one or more of Toll-like receptors, Src family kinases, NF-κB molecules, proteases or proteasomes.

Sun et al. (2007), *Zhongguo Zhong Yao Za Zhi*, 32(15): 1547-51 describe the effect of artemisinin pre-treatment on ischemia/reperfusion injury of isolated rat myocardium. Wang et al. (2011), *Invest Ophthalmol Vis Sci*, 52(2):916-9 describe the effect of artesunate on endotoxin-induced uveitis in rats. Li et al. (2008), *Int Immunopharmacol*, 8(3):379-89 describe the ability of artesunate to protect sepsis model mice against heat-killed *E. coli* challenge by decreasing TLR4, TLR9 mRNA expressions and transcription factor NF-κB activation.

The present inventors have surprisingly found that administration of artesunate and its related compounds can provide protection against organ damage caused by trauma haemorrhage, and also in stroke and burns injury. The present inventors have also surprisingly found that administration of artesunate and its related compounds can reduce the infarct size in MI and can even reduce the level of damage after the infarction has taken place.

Accordingly, in a first aspect of the invention there is provided a compound according to Formula I

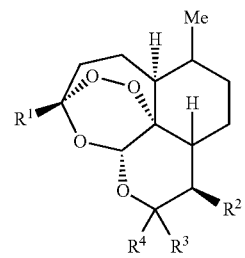

wherein $R^1$ and $R^2$ are independently H or an optionally substituted group selected from an alkyl, a heteroalkyl, an aryl, a heteroaryl, an arylalkyl, and a heteroarylalkyl, and $R^3$ and $R^4$ taken together form a carbonyl (=O); or wherein $R^1$ and $R^2$ are independently H or an optionally substituted group selected from an alkyl, a heteroalkyl, an aryl, a heteroaryl, an arylalkyl, and a heteroarylalkyl, $R^3$ is H and $R^4$ is H or —$OR^5$, wherein $R^5$ is H or an optionally substituted group selected from an alkyl, a heteroalkyl, an aryl, a heteroaryl, an arylalkyl, and a heteroarylalkyl; or a pharmaceutically acceptable salt or ester thereof for use in the treatment of trauma haemorrhage, trauma haemorrhage-induced organ injury, trauma haemorrhage-induced multiple organ failure, stroke or burns injury.

Trauma haemorrhage is also known as haemorrhagic shock. Trauma haemorrhage-induced organ injury includes trauma haemorrhage-induced pancreatitis, trauma haemorrhage-induced intestinal injury, trauma haemorrhage-induced brain injury, trauma haemorrhage-induced head injury, trauma haemorrhage-induced acute lung injury, trauma haemorrhage-induced spinal cord injury or trauma haemorrhage-induced adult respiratory distress syndrome (ARDS). References to burns injury include burns-associated multiple organ failure and burn-induced organ injury, such as burn-induced renal dysfunction or kidney disease/failure.

In one embodiment of the invention, in the compound according to Formula I, $R^1$ and $R^2$ are independently H or an optionally substituted $C_1$-$C_{10}$ alkyl and $R^3$ and $R^4$ taken together form a carbonyl (=O) group; or $R^1$ and $R^2$ are independently H or an optionally substituted $C_1$-$C_{10}$ alkyl, $R^3$ is H and $R^4$ is H or —$OR^5$, wherein $R^5$ is H or an optionally substituted group selected from an alkyl, a heteroalkyl, an aryl, a heteroaryl, an arylalkyl, and a heteroarylalkyl; or a pharmaceutically acceptable salt or ester thereof.

In another embodiment of the invention, in the compound according to Formula I, $R^1$ and $R^2$ are independently H or an optionally substituted $C_1$-$C_{10}$ alkyl, and $R^3$ and $R^4$ taken together form a carbonyl (=O) group, or a pharmaceutically acceptable salt or ester thereof In another embodiment of the invention, in the compound according to Formula I, $R^1$ and $R^2$ are independently H or an optionally substituted $C_1$-$C_{10}$ alkyl, $R^3$ is H and $R^4$ is H or —$OR^5$, wherein $R^5$ is H or an optionally substituted group selected from an alkyl, a heteroalkyl, an aryl, a heteroaryl, an arylalkyl, and a heteroarylalkyl; or a pharmaceutically acceptable salt or ester thereof.

In a further embodiment of the invention, in the compound according to Formula I, $R^1$ and $R^2$ are independently H or an optionally substituted $C_1$-$C_3$ alkyl, and $R^3$ and $R^4$ taken together form a carbonyl (=O) group; or $R^1$ and $R^2$ are independently H or an optionally substituted $C_1$-$C_3$ alkyl, $R^3$ is H and $R^4$ is H or —$OR^5$ wherein $R^5$ is H or an optionally substituted group selected from an alkyl, a heteroalkyl, an aryl, a heteroaryl, an arylalkyl, and a heteroarylalkyl; or a pharmaceutically acceptable salt or ester thereof.

In a further embodiment of the invention, in the compound according to Formula I, $R^1$ and $R^2$ are independently H or an optionally substituted methyl, and $R^3$ and $R^4$ taken together form a carbonyl (=O) group; or $R^1$ and $R^2$ are independently H or an optionally substituted methyl, $R^3$ is H and $R^4$ is —$OR^5$, wherein $R^5$ is H or an optionally substituted group selected from an alkyl, a heteroalkyl, an aryl, a heteroaryl, an arylalkyl, and a heteroarylalkyl; or a pharmaceutically acceptable salt or ester thereof.

In a further embodiment of the invention, in the compound according to Formula I, $R^1$ and $R^2$ are both independently methyl (—$CH_3$), and $R^3$ and $R^4$ taken together form a carbonyl (=O) group; or $R^1$ and $R^2$ are both methyl, $R^3$ is H and $R^4$ is —$OR^5$, wherein $R^5$ is H or an optionally substituted group selected from an alkyl, an aryl, a heteroalkyl, a heteroaryl, an arylalkyl, and a heteroarylalkyl; or a pharmaceutically acceptable salt or ester thereof.

In a further embodiment of the invention, in the compound according to Formula I, $R^1$ and $R^2$ are both an optionally substituted methyl, and $R^3$ and $R^4$ taken together form a carbonyl (=O) group; or $R^1$ and $R^2$ are both methyl, $R^3$ is H and $R^4$ is —$OR^5$, wherein $R^5$ is selected from the group consisting of H, —$CH_3$, —$CH_2CH_3$, —$CO(CH_2)_2COOH$ and —$CH_2C_6H_4COOH$.

In some embodiments, $R^5$ is H, an alkyl, or an arylalkyl, wherein the alkyl and/or arylalkyl is/are optionally substituted with one more or more of halo, =O, $COOR^6$, $OR^6$ and $OCOR^6$, wherein $R^6$ is H or a $C_1$-$C_6$ alkyl. For example, in one embodiment of the invention, in the compound according to Formula I, $R^1$ and $R^2$ are both a methyl, and $R^3$ and $R^4$ taken together form a carbonyl (=O) group; or $R^1$ and $R^2$ are both methyl, $R^3$ is H and $R^4$ is —$OR^5$ wherein $R^5$ is H, an alkyl, or an arylalkyl, wherein the alkyl and/or arylalkyl is/are optionally substituted with one more or more of halo, =O, $COOR^6$, $OR^6$ and $OCOR^6$, wherein $R^6$ is H or a $C_1$-$C_6$ alkyl.

In some embodiments of the invention, $R^5$ may be selected from the group consisting of H, —$CH_3$, —$CH_2CH_3$, —$CO(CH_2)_2COOH$ and —$CH_2C_6H_4COOH$.

In some embodiments $R^5$ comprises a carboxyl and optionally the compounds of Formula I are used as salts or esters of the carboxylic acid. In some embodiments, the ester is a simple alkyl ester such as a $C_1$-$C_6$ alkyl ester, where the $C_1$-$C_6$ alkyl is optionally substituted with one or more halo, hydroxyl, or $C_1$-$C_4$ alkoxy groups. Where the compound of Formula I is an ester, it is sometimes a methyl or ethyl or propyl or butyl ester, or a 2-methoxyethyl ester or an ethylene glycol ester.

As used herein, the terms "alkyl," "alkenyl" and "alkynyl" include straight-chain, branched-chain and cyclic monovalent hydrocarbyl radicals, and combinations of these, which contain only C and H when they are unsubstituted. Examples include methyl, ethyl, isobutyl, cyclohexyl, cyclopentylethyl, 2-propenyl, 3-butynyl, and the like. The total number of carbon atoms in each such group is sometimes described herein, e.g., when the group can contain up to ten carbon atoms it can be represented as $C_{1-10}$. When heteroatoms (N, O and S, for example) replace carbon atoms as in heteroalkyl groups, for example, the numbers describing the group, though still written as e.g. $C_1$-$C_6$, represent the sum of the number of carbon atoms in the group plus the number of such heteroatoms that are included as replacements for carbon atoms in the ring or chain being described.

In some embodiments, the alkyl, alkenyl and alkynyl groups of the invention are $C_1$-$C_{10}$ (alkyl) or $C_2$-$C_{10}$ (alkenyl or alkynyl). Alternatively, they are $C_1$-$C_8$ (alkyl) or $C_2$-$C_8$ (alkenyl or alkynyl). Sometimes they are $C_1$-$C_4$ (alkyl) or $C_2$-$C_4$ (alkenyl or alkynyl). A single group can include more than one type of multiple bond, or more than one multiple bond; such groups are included within the definition of the term "alkenyl" when they contain at least one carbon-carbon double bond, and are included within the term "alkynyl" when they contain at least one carbon-carbon triple bond.

Typical optional substituents on an alkyl, alkenyl or alkynyl group include, but are not limited to, halo, =O, =N—CN, =N—OR, =NR, OR, $NR_2$, SR, $SO_2R$, $SO_2NR_2$, $NRSO_2R$, $NRCONR_2$, NRCOOR, NRCOR, CN, COOR, $CONR_2$, OCOR, COR, and $NO_2$, wherein each R is independently H, $C_1$-$C_8$ alkyl, $C_2$-$C_8$ heteroalkyl, $C_1$-$C_8$ acyl, $C_2$-$C_8$ heteroacyl, $C_2$-$C_8$ alkenyl, $C_2$-$C_8$ heteroalkenyl, $C_2$-$C_8$ alkynyl, $C_2$-$C_8$ heteroalkynyl, $C_6$-$C_{10}$ aryl, or $C_5$-$C_{10}$ heteroaryl, and each R is optionally substituted with halo, =O, =N—CN, =N—OR', =NR', OR', $NR'_2$, SR', $SO_2R'$, $SO_2NR'_2$, $NR'SO_2R'$, $NR'CONR'_2$, NR'COOR', NR'COR', CN, COOR', $CONR'_2$, OOCR', COR', and $NO_2$, wherein each R' is independently H, $C_1$-$C_8$ alkyl, $C_2$-$C_8$ heteroalkyl, $C_1$-$C_8$ acyl, $C_2$-$C_8$ heteroacyl, $C_6$-$C_{10}$ aryl or $C_5$-$C_{10}$ heteroaryl. Alkyl, alkenyl and alkynyl groups can also be substituted by $C_1$-$C_8$ acyl, $C_2$-$C_8$ heteroacyl, $C_6$-$C_{10}$ aryl or $C_5$-$C_{10}$ heteroaryl, each of which can be substituted by the substituents that are appropriate for the particular group. In some embodiments, the alkyl, alkenyl or alkynyl groups are substituted with one more or more of halo, =O, COOR$^6$, OR$^6$ and OCOR$^6$, wherein R$^6$ is H or a $C_1$-$C_6$ alkyl.

While "alkyl" as used herein includes cyclo-alkyl and cyclo-alkylalkyl groups, the term "cyclo-alkyl" may be used herein to describe a carbo-cyclic non-aromatic group that is connected via a ring carbon atom (i.e., its open valence for connecting to a molecule is on a ring carbon), and "cyclo-alkylalkyl" may be used to describe a carbocyclic non-aromatic group that is connected to the molecule through an alkylene linker. Similarly, "heterocyclyl" may be used to describe a non-aromatic cyclic group that contains at least one heteroatom as a ring member and that is connected to the molecule via a ring atom, which may be C or N; and "heterocyclylalkyl" may be used to describe such a group that is connected to another molecule through a linker. The sizes and substituents that are suitable for the cycloalkyl, cycloalkylalkyl, heterocyclyl, and heterocyclylalkyl groups are the same as those described above for alkyl groups. As used herein, these terms also include rings that contain a double bond or two, as long as the ring is not aromatic.

As used herein, "acyl" encompasses groups comprising an alkyl, alkenyl, alkynyl, aryl or arylalkyl radical attached at one of the two available valence positions of a carbonyl carbon atom (—C(O)—), and heteroacyl refers to the corresponding groups wherein at least one carbon other than the carbonyl carbon has been replaced by a heteroatom, for example chosen from N, O and S. The other open valence of the carbonyl is available to connect the acyl group or heteroacyl group to a base molecule. Thus heteroacyl includes, for example, —C(=O)OR and —C(=O)NR$_2$ as well as —C(=O)— heteroaryl.

Acyl and heteroacyl groups are bonded to any group or molecule to which they are attached through the open valence of the carbonyl carbon atom. In some embodiments, they are $C_1$-$C_8$ acyl groups, which include formyl, acetyl, pivaloyl, and benzoyl, and $C_2$-$C_8$ heteroacyl groups, which include methoxyacetyl, ethoxycarbonyl, and 4-pyridinoyl. The hydrocarbyl groups, aryl groups, and heteroforms of such groups that comprise an acyl or heteroacyl group can be substituted with the substituents described herein as generally suitable substituents for each of the corresponding component of the acyl or heteroacyl group.

"Aromatic" moiety or "aryl" moiety refers to a monocyclic or fused bicyclic moiety having the well-known characteristics of aromaticity; examples include phenyl and naphthyl. Similarly, "heteroaromatic" and "heteroaryl" refer to such monocyclic or fused bicyclic ring systems which contain as ring members one or more heteroatoms, for example selected from O, S and N. The inclusion of a heteroatom permits aromaticity in 5-membered rings as well as 6-membered rings. Typical heteroaromatic systems include monocyclic $C_5$-$C_6$ aromatic groups such as pyridyl, pyrimidyl, pyrazinyl, thienyl, furanyl, pyrrolyl, pyrazolyl, thiazolyl, oxazolyl, and imidazolyl and the fused bicyclic moieties formed by fusing one of these monocyclic groups with a phenyl ring or with any of the heteroaromatic monocyclic groups to form a $C_8$-$C_{10}$ bicyclic group such as indolyl, benzimidazolyl, indazolyl, benzotriazolyl, isoquinolyl, quinolyl, benzothiazolyl, benzofuranyl, pyrazolopyridyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity. In some embodiments, the ring systems contain 5-12 ring member atoms. In some embodiments, the monocyclic heteroaryls may contain 5-6 ring members, and the bicyclic heteroaryls contain 8-10 ring members.

Aryl and heteroaryl moieties may be substituted with a variety of substituents including $C_1$-$C_8$ alkyl, $C_2$-$C_8$ alkenyl, $C_2$-$C_8$ alkynyl, $C_5$-$C_{12}$ aryl, $C_1$-$C_8$ acyl, and heteroforms of these, each of which can itself be further substituted; other substituents for aryl and heteroaryl moieties include halo, OR, NR$_2$, SR, SO$_2$R, SO$_2$NR$_2$, NRSO$_2$R, NRCONR$_2$, NRCOOR, NRCOR, CN, COOR, CONR$_2$, OCOR, COR, and NO$_2$, wherein each R is independently H, $C_1$-$C_8$ alkyl, $C_2$-$C_8$ alkenyl, $C_2$-$C_8$ alkynyl, $C_6$-$C_{10}$ aryl, $C_5$-$C_{10}$ heteroaryl, $C_7$-$C_{12}$ arylalkyl, or $C_6$-$C_{12}$ heteroarylalkyl, and each R is optionally substituted as described above for alkyl groups. In some embodiments, they are substituted with one more or more of halo, =O, COOR$^6$, OR$^6$ and OCOR$^6$, wherein R$^6$ is H or a $C_1$-$C_6$ alkyl. The substituent groups on an aryl or heteroaryl group may of course be further substituted with the groups described herein as suitable for each type of such substituents or for each component of the substituent. Thus, for example, an arylalkyl substituent may be substituted on the aryl portion with substituents described herein as typical for aryl groups, and it may be further substituted on the alkyl portion with substituents described herein as typical or suitable for alkyl groups.

Similarly, "arylalkyl" and "heteroarylalkyl" refer to aromatic and heteroaromatic ring systems which are bonded to their attachment point through a linking group such as an alkylene, including substituted or unsubstituted, saturated or unsaturated, cyclic or acyclic linkers. The linker may be $C_1$-$C_8$ alkyl or a hetero form thereof. These linkers may also include a carbonyl group, thus making them able to provide substituents as an acyl or heteroacyl moiety. An aryl or heteroaryl ring in an arylalkyl group may be substituted with the same substituents described above for aryl groups. An arylalkyl group may include a phenyl ring optionally substituted with the groups defined above for aryl groups and a $C_1$-$C_4$ alkylene that is unsubstituted or is substituted with one or two $C_1$-$C_4$ alkyl groups, where the alkyl groups can optionally cyclize to form a ring such as cyclopropane, dioxolane, or oxacyclopentane. Similarly, a heteroarylalkyl group may include a $C_5$-$C_6$ monocyclic heteroaryl group that is optionally substituted with the groups described above as substituents typical on aryl groups and a $C_1$-$C_4$ alkylene that is unsubstituted or is substituted with one or two $C_1$-$C_4$ alkyl groups, or it includes an optionally substituted phenyl ring or $C_5$-$C_6$ monocyclic heteroaryl and a $C_1$-$C_4$ heteroalkylene that is unsubstituted or is substituted with one or two $C_1$-$C_4$ alkyl groups, where the alkyl groups can optionally cyclize to form a ring such as cyclopropane, dioxolane, or oxacyclopentane.

Where an arylalkyl group is described as optionally substituted, the substituents may be on either the alkyl portion or on the aryl or heteroaryl portion of the group. The substituents optionally present on the alkyl portion are the same as those described above for alkyl groups generally; the substituents optionally present on the aryl or heteroaryl portion are the same as those described above for aryl groups generally. In some embodiments, the arylalkyl or heteroarylalkyl are substituted with one more or more of halo, =O, COOR$^6$, OR$^6$ and OCOR$^6$, wherein R$^6$ is H or a $C_1$-$C_6$ alkyl.

"Arylalkyl" groups as used herein are hydrocarbyl groups if they are unsubstituted, and are described by the total number of carbon atoms in the ring and alkylene or similar linker. Thus a benzyl group is a $C_7$-arylalkyl group, and phenylethyl is a $C_8$-arylalkyl.

"Alkylene" as used herein refers to a divalent hydrocarbyl group; because it is divalent, it can link two other groups together. Sometimes it refers to —$(CH_2)_n$— where n is 1-8 and suitably n is 1-4, though where specified, an alkylene can also be substituted by other groups, and can be of other lengths. The open valences of an alkylene need not be at opposite ends of a chain. Thus —CH(Me)- and —C(Me)$_2$- are also included within the scope of the term "alkylenes", as are cyclic groups such as cyclopropan-1,1-diyl. Where an alkylene group is substituted, the substituents include those typically present on alkyl groups as described herein.

In general, any alkyl, alkenyl, alkynyl, acyl, or aryl or arylalkyl group or any heteroform of one of these groups that is contained in a substituent may itself optionally be substituted by additional substituents. The nature of these substituents is similar to those recited with regard to the primary substituents themselves if the substituents are not otherwise described. Thus, where an embodiment of, for example, R' is alkyl, this alkyl may optionally be substituted by the remaining substituents listed as embodiments for R' where this makes chemical sense, and where this does not undermine the size limit provided for the alkyl per se; e.g., alkyl substituted by alkyl or by alkenyl would simply extend the upper limit of carbon atoms for these embodiments. However, alkyl substituted by aryl, amino, alkoxy, =O, and the like would be included within the scope of the invention, and the atoms of these substituent groups are not counted in the number used to describe the alkyl, alkenyl, etc. group that is being described. Where no number of substituents is specified, each such alkyl, alkenyl, alkynyl, acyl, or aryl group may be substituted with a number of substituents according to its available valences; in particular, any of these groups may be substituted with fluorine atoms at any or all of its available valences, for example.

"Optionally substituted" as used herein indicates that the particular group or groups being described may have no non-hydrogen substituents, or the group or groups may have one or more non-hydrogen substituents. If not otherwise specified, the total number of such substituents that may be present is equal to the number of H atoms present on the unsubstituted form of the group being described, in some embodiments, the number of substituents permitted on a group is equal to the number of carbon atoms in the group. Where an optional substituent is attached via a double bond, such as a carbonyl oxygen (=O), the group occupies two available valences, so the total number of other substituents that may be included is reduced according to the number of other available valences.

"Halo" as used herein includes fluoro, chloro, bromo and iodo. "Hetero" atoms may be selected from the group consisting of nitrogen, oxygen, sulphur, phosphorus, boron, chlorine, bromine and iodine. Suitable, the heteroatom is selected from the group consisting of nitrogen, oxygen and sulphur.

Exemplary compounds according to Formula I include artesunate, artemisinin, artemether, dihydroartemisinin (also known as DHA or artenimol), artelinic acid and artemotil (also know as arteether). The compounds may be in the alpha or beta forms (in reference to the stereoisomerism of $R^3$ and $R^4$).

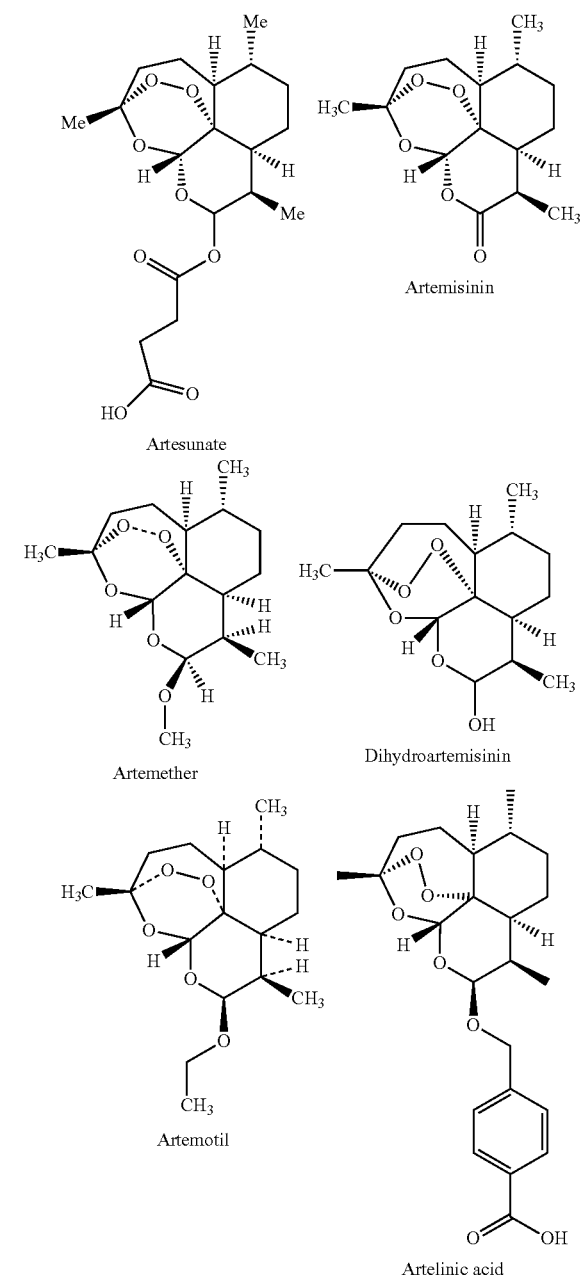

Artesunate

Artemisinin

Artemether

Dihydroartemisinin

Artemotil

Artelinic acid

The systematic (International Union of Pure and Applied Chemistry, IUPAC) name of artemisinin is (3R,5aS,6R,8aS,9R,12S,12aR)-octahydro-3,6,9-trimethyl-3,12-epoxy-12H-pyrano[4,3-j]-1,2-benzodioxepin-10(3H)-one. The systematic (IUPAC) name of dihydroartemisinin is (3R,5aS,6R,8aS,9R,12S,12aR)-decahydro-3,6,9-trimethyl-3,12-epoxy-12H-pyrano[4,3-j]-1,2-benzodioxepin-10-ol. The systematic (IUPAC) name of artelinic acid is 4-[(3R,5aS,6R,8aS,9R,10S,12R,12aR)-decahydro-3,6,9-trimethyl-3,12-epoxy-12H-pyrano[4,3-j]-1,2-benzodioxepin-10-yl]oxy]methylbenzoic acid. For brevity, references to "compounds of Formula I" include the preferred narrower definitions provided above, including the specific compounds disclosed herein (such as artesunate, artemisinin, artemether, dihydroartemisinin, artelinic acid and artemotil).

Accordingly, in one embodiment of the invention there is provided artemisinin or derivatives thereof, or pharmaceutically acceptable salts or esters thereof, for use in the treatment of trauma haemorrhage, trauma haemorrhage-induced organ injury, trauma haemorrhage-induced multiple organ failure, stroke or burns injury. In one embodiment, the artemisinin derivatives are selected from the group consisting of artesunate, artemether, dihydroartemisinin, artelinic acid and artemotil.

In embodiments of the invention, the compounds of Formula I, or a pharmaceutically acceptable salt or ester thereof, may be provided for use in the treatment of trauma haemorrhage-induced organ injury such as pancreatitis, intestinal injury, brain injury, head injury, acute lung injury, spinal cord injury, adult respiratory distress syndrome (ARDS), and also for use in the treatment of traumatic injuries such as traumatic head injury and traumatic brain injury.

Traumatic brain injury is also known as intracranial injury and occurs when an external force traumatically injures the brain. Damage to the brain can be focal (confined to specific areas of the brain) or diffuse (damage may be distributed in a more general manner), although it is common for both types of injury to exist in a given case. Traumatic head injury is injury to the head that may or may not include damage to the brain. Generally, in embodiments of the invention, traumatic head or traumatic brain injury is trauma haemorrhage-induced traumatic head injury or trauma haemorrhage-induced brain injury.

Pancreatitis refers to inflammation of the pancreas and may be acute pancreatitis or chronic pancreatitis. Generally, in embodiments of the invention, the pancreatitis is trauma haemorrhage-induced pancreatitis.

The acute lung injury is generally secondary acute lung injury as a result of trauma haemorrhage or associated conditions. In acute lung injury, the capillary-endothelial interface is disrupted, resulting in the creation of an open interface between the lung and the blood, facilitating the spread of micro-organisms from the lung systemically and causing a systemic inflammatory response. Moreover, the injury to epithelial cells compromises the lung's ability to pump fluid out of airspaces. Fluid filled airspaces, loss of surfactant, microvascular thrombosis and disorganized repair (which can lead to fibrosis) reduces resting lung volumes (decreased compliance), increasing ventilation-perfusion mismatch, right to left shunt and the work of breathing. Generally, in embodiments of the invention, the acute lung injury is trauma haemorrhage-induced acute lung injury Adult respiratory distress syndrome (ARDS) is also known as acute respiratory distress syndrome. It is characterized by inflammation of the lung parenchyma leading to impaired gas exchange with concomitant systemic release of inflammatory mediators causing inflammation, hypoxemia and frequently resulting in multiple organ failure. Generally, in embodiments of the invention, the ARDS is trauma haemorrhage-induced ARDS.

The present invention also relates to burns and burns injuries and associated disorders. Burns are injury to the flesh caused by heat (direct heat or hot liquids), electricity, chemicals, light, radiation or friction. "Burns" within the concept of this invention therefore extends to all types of burn injury, although in particular to burns caused by heat, hot liquids, electricity and radiation. Burns are classified according to the extent of damage caused. First degree burns result in damage to the epidermis only. Second degree burns may extend into the superficial (papillary) dermis or further into the deep (reticular) dermis. Secondary superficial partial thickness burns may be complicated by local infection and/or cellulitis. Secondary deep partial thickness burns may be complicated by scarring and contractures that may require excision and/or skin grafting. Third degree burns (full thickness burns) involve the entire dermis and usually require excision of the damaged tissue. Fourth degree burns extend through the skin, subcutaneous tissue and into the underlying muscle or bone. Excision is of the damaged tissue is required.

Burns may also be classified according to the percentage of the total body surface area that is damaged. Burns of 10% or more in children and 15% or more in adults are potentially life threatening injuries because of the risk of hypovolaemic shock.

The present inventors have found that compounds of Formula I, or pharmaceutically acceptable salts or esters thereof, are useful in the treatment of burns. Accordingly, in one aspect of the invention there is provided a compound of Formula I for use in the treatment of burns, including chemical burns, electrical burns, radiation burns, friction burns and scalds. This aspect of the invention also extends to methods of treating burns by administering a compound of Formula I, or a pharmaceutically acceptable salt or ester thereof, to a patient in need thereof. There is also provided a compound of Formula I (or its derivatives) for use in the treatment of trauma haemorrhage-induced burns injury and burn-induced organ injury, such as burn-induced renal dysfunction, and corresponding methods of treatment.

The present invention also relates to the treatment of strokes. Strokes (also known as cerebrovascular accidents, CVAs) occur when the blood supply to the brain is interrupted. Stokes can be ischaemic, when an artery supplying blood to part of the brain is blocked (for example due to thrombosis), or haemorrhagic, when a blood vessel bursts and bleeds into the brain itself or on the surface of the brain between the brain and the skull. In particular embodiments of the invention, the strokes treated using the compounds of Formula I or its derivatives are ischaemic strokes.

Risk factors for stroke include old age, hypertension, diabetes, high cholesterol, cigarette smoking and atrial fibrillation. The term "stroke" as used herein is intended to include transient ischemic attacks (TIAs), which is a transient episode of neurological dysfunction caused by ischaemia without acute infarction. Strokes are considered a medical emergency and therefore medicaments that can reduce the damage caused by strokes are highly desired in the art. The term "stroke" as used herein is also intended to include ischaemia-reperfusion caused by occlusion (either transient or permanent) of a cerebral or extra cerebral vessel that supplies the brain with blood and its subsequent reperfusion, or rupture with haemorrhage of such vessels with brain oedema, or injury as a result of brain oedema caused by any other factors.

The present inventors have found that the administration of a compound according to Formula I, or a pharmaceutically acceptable salt or ester thereof, can reduce the damage caused by strokes, in particular ischaemic stokes. Accordingly, in one aspect of the invention there is provided a compound of Formula I for use in the treatment of stroke, ischaemic strokes, haemorrhagic strokes and transient ischemic attacks (TIAs). This aspect of the invention also extends to methods of treating strokes by administering a compound of Formula I, or a pharmaceutically acceptable salt or ester thereof, to a patient in need thereof.

The compounds used in the present invention can be obtained by any suitable means known to a person of skill in the art. For example, Ro et al. (2006), *Nature,* 440(7086): 940-3 describe the production of the antimalarial precursor artemisinic acid in engineered yeast. Van Herpen et al.

(2010), *PLoS One,* 5(12):e14222 describe an engineered form of *Nicotiana benthamiana* that can be used to make artemisinic acid. Alternatively, artemisinin may be obtained from the plant *Artemisia annua* L. (Qinghao) by any suitable means known to a person of skill in the art, for example as described in Kohler et al, (1997), *J Chromatogr A,* 785(1-2):353-60. US2008/0139642 also describes the preparation of artemisinin derivatives.

Artesunate can also be prepared from dihydroartemisinin (DHA, the active metabolite of artemisinin compounds) by reacting it with succinic acid anhydride in basic medium. Pyridine as base/solvent, sodium bicarbonate in chloroform and catalyst DMAP (N,N-dimethylaminopyridine) and triethylamine in 1,2-dichloroethane can be used, with yields of up to 100%. A large scale process may involve treatment of DHA in dichloromethane with a mixture of pyridine, a catalytic amount of DMAP and succinic anhydride. The dichloromethane mixture is stirred for 6-9 h to get artesunate in quantitative yield. The product can be further re-crystallized from dichloromethane. alpha-Artesunate is usually formed (melting point 135-137° C.).

Other means for obtaining artemisinin and its derivates will be apparent to a person of skill in the art. Artemisinin and derivatives thereof, such as dihydroartemisinin, are also available from suppliers such as Sigma-Aldrich (Poole, Dorset, U.K.).

In embodiments of the invention, a compound of Formula I, or salts or derivatives thereof, may be administered in combination with one or more pharmaceutically active agents.

In a second aspect of the invention there is provided a pharmaceutical composition comprising a compound of Formula I, or salts or derivatives thereof, and a pharmaceutically acceptable excipient for use in the treatment of trauma haemorrhage, trauma haemorrhage-induced organ injury, trauma haemorrhage-induced multiple organ failure, stroke or burns injury.

Pharmaceutically acceptable excipients include binders, fillers, coatings, disintegrants, solubilisers and solvents.

The compounds of Formula I may be present in the form of a pharmaceutically acceptable salt, for example, hydrochloride (HCl), mesylate, maleate, chloride, bromide, citrate, tartrate, sulphate, phosphate, including any suitable cation (sodium, calcium, benzathine, magnesium, ammonium, zinc, potassium, and so on). Many of the compounds of Formula I may include a carboxylic acid group; for such compounds, a salt can be formed by de-protonation of the carboxylic acid to form a carboxylate.

The pharmaceutical compositions may include one or more further pharmaceutically active agents.

The pharmaceutical compositions may be adapted for administration by any route considered suitable to a person of skill in the art. For example, the pharmaceutical composition may be adapted for oral (including buccal or sublingual), parenteral, intravenous, intramuscular, intrathecal or intraperitoneal administration, or for administration by inhalation. Such compositions may be prepared by any method known in the art of pharmacy, for example by admixing the active ingredient with the carrier(s) or excipient(s) under sterile conditions.

Pharmaceutical compositions adapted for oral administration may be presented as discrete units such as capsules or tablets; as powders or granules; as solutions, syrups or suspensions (in aqueous or non-aqueous liquids; or as edible foams or whips; or as emulsions). Dihydroartemisinin (DHA) may be particularly useful for oral administration since it is lipid soluble.

Suitable excipients for tablets or hard gelatine capsules include lactose, maize starch or derivatives thereof, stearic acid or salts thereof. Suitable excipients for use with soft gelatine capsules include for example vegetable oils, waxes, fats, semi-solid, or liquid polyols etc.

For the preparation of solutions and syrups, excipients which may be used include for example water, polyols and sugars. For the preparation of suspensions oils (e.g. vegetable oils) may be used to provide oil-in-water or water in oil suspensions.

Pharmaceutical compositions adapted for administration by inhalation include fine particle dusts or mists which may be generated by means of various types of metered dose pressurised aerosols, nebulizers or insufflators.

Pharmaceutical compositions adapted for parenteral administration include aqueous and non-aqueous sterile injection solution which may contain anti-oxidants, buffers, bacteriostats and solutes which render the formulation substantially isotonic with the blood of the intended recipient; and aqueous and non-aqueous sterile suspensions which may include suspending agents and thickening agents. Excipients which may be used for injectable solutions include water, alcohols, polyols, glycerine and vegetable oils, for example. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules and tablets.

The pharmaceutical compositions may contain preserving agents, solubilising agents, stabilising agents, wetting agents, emulsifiers, sweeteners, colourants, odourants, salts (substances of the present invention may themselves be provided in the form of a pharmaceutically acceptable salt), buffers, coating agents or antioxidants. They may also contain therapeutically active agents in addition to the substance of the present invention.

When preparing any compositions of the invention comprising a compound of Formula I, a person of skill in the art may take any necessary steps to increase the solubility of the compounds of Formula I. For example, the compounds of Formula I may be present in the form of an inclusion complex, such as a cyclodextrin inclusion complex, as described in Ansari et al. (2009), *Arch Pharm Res Vol.,* 32(1):155-65. According, a compound of Formula I may be present in the form of an inclusion complex, for example a cyclodextrin inclusion complex or a hydroxypropyl-β-cyclodextrin complex. Other techniques for increasing the solubility would be apparent to a person of skill in the art, for example the use of surfactants (such as sodium lauryl sulphate) and co-solvents (such as ethanol or DMSO).

Dosages of the pharmaceutical compositions of the present invention can vary between wide limits, depending upon the disease or disorder to be treated, the age and condition of the individual to be treated, etc. and a physician will ultimately determine appropriate dosages to be used. For example, a compound of Formula I, or a pharmaceutically acceptable salt or ester thereof, may be administered in an amount of 0.1 to 50 mg/kg, or 0.1 to 30 mg/kg, or between 0.1 and 3 mg/kg, or between 0.3 and 3 mg/kg. In some embodiments, the artesunate is administered in amount equal to or less than 50, 30, 25, 20, 15, 10, 5 or 1 mg/kg. The compound of Formula I, or a pharmaceutically acceptable salt or ester thereof, may be administered at these dosages only once. Alternatively, a compound of Formula I, or a pharmaceutically acceptable salt or ester thereof, may be administered at these dosages once per day, twice per day, three times per day, four times per day five times per day, wherein preferably each bolus is less than the dosages specified above (rather than a cumulative dosage for the whole day). In some embodiments, the compounds are administered no more that three times per day, or no more than two times per day, or only once per day. In some embodiments, the dosages are given at least 6 hours apart, preferably at least 12 hours apart. The compounds may be administered as a bolus or alternatively may be administered over a period of time as deemed suitable by a skilled person, for example by intravenous drip. In some embodiments, the compounds of Formula I, or pharmaceutically acceptable salts or esters thereof, may be administered in an amount of between 0.1 and 5 mg/kg (or between 0.1 and 3 mg/kg) as a single bolus dose, or once per day, or twice per day, or three times per day, or more.

Such compositions may be formulated for human or for veterinary medicine. The present applications should be interpreted as applying equally to humans as well as to animals, unless the context clearly implies otherwise.

In a third aspect of the invention there is provided the use of a compound of Formula I, or a pharmaceutically acceptable salt or ester thereof, in the manufacture of a medicament for the treatment of trauma haemorrhage, trauma haemorrhage-induced organ injury, trauma haemorrhage-induced multiple organ failure, stroke or burns injury. In another aspect of the invention there is provided the use of artemisinin and derivatives thereof, or a pharmaceutically acceptable salt or ester thereof, for use in the manufacture of a medicament for the treatment of trauma haemorrhage, trauma haemorrhage-induced organ injury, trauma haemorrhage-induced multiple organ failure, stroke or burns injury. In one embodiment, the artemisinin derivatives are selected from the group consisting of artesunate, artemether, dihydroartemisinin, artelinic acid and artemotil.

In a fourth aspect of the invention there is provided a kit of parts comprising a compound of Formula I, or a pharmaceutically acceptable salt or ester thereof, and one or more further pharmaceutically active agent for simultaneous, separate or sequential administration. The kit of parts may optionally include instructions for use. The compound of Formula I may be present in a unit-dosage form.

In a fifth aspect of the invention there is provided a resuscitation solution (alternatively a reperfusion solution) comprising a compound of Formula I, or a pharmaceutically acceptable salt or ester thereof, and one or more volume expanders.

In one embodiment, the volume expander is a crystalloid or a colloid, or a combination of a crystalloid and a colloid.

A crystalloid is an aqueous solution of salts comprising at least two ions selected from the group consisting of sodium ions, chloride ions, lactate ions, potassium ions and calcium ions. In some embodiments, the crystalloid is an aqueous solution comprising at least three ions selected from the group consisting of sodium ions, chloride ions, lactate ions, potassium ions and calcium ions. In some embodiments, the crystalloid is an aqueous solution comprising at least four ions selected from the group consisting of sodium ions, chloride ions, lactate ions, potassium ions and calcium ions. In some embodiments, the crystalloid is an aqueous solution comprising sodium ions, chloride ions, lactate ions, potassium ions and calcium ions. The crystalloid may also comprise bicarbonate ions and/or glucose.

Example crystalloids include aqueous solutions of mineral salts (such a saline, Ringer's lactate or Hartmann's solution) or other water-soluble molecules. One liter of Ringer's lactate solution (also known as lactated Ringer's solution or Ringer's Lactate) generally contains:
about 130 mEq of sodium ions=130 mmol/L
about 109 mEq of chloride ions=109 mmol/L
about 28 mEq of lactate=28 mmol/L
about 4 mEq of potassium ions=4 mmol/L
about 3 mEq of calcium ions=1.5 mmol/L Generally, the sodium, chloride, potassium and lactate comes from NaCl (sodium chloride), $NaC_3H_5O_3$ (sodium lactate), $CaCl_2$ (calcium chloride), and KCl (potassium chloride). However, it would be apparent to a person of skill in the art that other components could be used to reach the desired ion concentrations. The pH of Ringer's lactate can be in the range of 6 to 7, for example 6.5, although it is generally an alkalizing solution.

One liter of Hartmann's solution (also known as compound sodium lactate) can contain:
131 mEq of sodium ions=131 mmol/L.
111 mEq of chloride ions=111 mmol/L.
29 mEq of lactate=29 mmol/L.
5 mEq of potassium ions=5 mmol/L.
4 mEq of calcium ions=2 mmol/L Accordingly, in one embodiment of the invention, the resuscitation solution of the invention comprises a compound of Formula I, or a pharmaceutically acceptable salt or ester thereof, and a crystalloid volume expander, wherein the crystalloid volume expander is an aqueous solution comprising at least three ions selected from the group consisting of sodium ions, chloride ions, lactate ions, potassium ions and calcium ions. In another embodiment of the invention, the resuscitation solution of the invention comprises a compound of Formula I, or a pharmaceutically acceptable salt or ester thereof, and a crystalloid volume expander, wherein the crystalloid volume expander is an aqueous solution comprising at least four ions selected from the group consisting of sodium ions, chloride ions, lactate ions, potassium ions and calcium ions. In a further embodiment of the invention, the resuscitation solution of the invention comprises a compound of Formula I, or a pharmaceutically acceptable salt or ester thereof, and a crystalloid volume expander, wherein the crystalloid volume expander is an aqueous solution comprising sodium ions, chloride ions, lactate ions, potassium ions and calcium ions.

In these embodiments, the ions may be present at any suitable concentration known to the skilled person. For example, the sodium ions may be present in a concentration of about 100 mmol/L to about 150 mmol/L. The chloride ions may be present in a concentration of about 90 mmol/L to about 120 mmol/L. The lactate ions may be present in a concentration of about 20 mmol/L to about 30 mmol/L. The potassium ions may be present in a concentration of about 2 mmol/L to about 6 mmol/L. The calcium ions may be present in a concentration of about 1 mmol/L to 5 about mmol/L. Bicarbonate ions (if present) may be present in a concentration of about 10 mmol/L to about 50 mmol/L. Glucose (if present) may be present at a concentration of about 2% to about 10% by weight, for example about 3% to about 6% by weight.

Accordingly, in another embodiment of the invention, the resuscitation solution of the invention comprises a compound of Formula I, or a pharmaceutically acceptable salt or ester thereof, in an aqueous solution comprising:
about 100 mmol/L to about 150 mmol/L of sodium ions
about 90 mmol/L to about 120 mmol/L of chloride ion about 20 mmol/L to about 30 mmol/L of lactate
about 2 mmol/L to about 6 mmol/L of potassium ions
about 1 mmol/L to about 5 mmol/L of calcium ions As will be apparent to the skilled person, the above aqueous solution is an example of a suitable crystalloid volume expander.

The resuscitation solution may alternatively include a colloid volume expander, or it may contain a mixture of the crystalloid volume expander described above and a colloid volume expander.

Examples of suitable colloids include gelatin, succinylated gelatin, albumin, dextran (for example dextran 40, dextran 70 or dextran 75), blood, or etherified starch (also known as hydroxyethyl starch, tetrastarch, hetastarch or pentastarch). The colloids are generally aqueous solutions comprising these components. For example, the colloid may comprise at least one component selected from the groups consisting of gelatin, succinylated gelatin, albumin, dextran, blood and etherified starch.

Commercially available colloids include Haemaccel® (Piramal, containing degraded gelatin polypeptides cross-linked via urea bridges), Gelofusine® (Braun, succinylated gelatin (modified fluid gelatin, average molecular weight 30 000) 40 g (4%), Na+154 mmol, Cl− 120 mmol/liter), Gelopasma® (Fresenius Kabi, partially hydrolysed and succinylated gelatin (modified liquid gelatin) (as anhydrous gelatin) 30 g (3%), $Na^+$ 150 mmol, $K^+$ 5 mmol, $Mg^{2+}$ 1.5 mmol, $Cl^−$ 100 mmol, lactate 30 mmol/liter), Isoplex® (Beacon, succinylated gelatin (modified fluid gelatin, average molecular weight 30 000) 40 g (4%), $Na^+$ 145 mmol, $K^+$4 mmol, $Mg^{2+}$ 0.9 mmol, $Cl^−$ 105 mmol, lactate 25 mmol/liter), Volplex® (Beacon, succinylated gelatin (modified fluid gelatin, average molecular weight 30 000) 40 g (4%), $Na^+$ 154 mmol, $Cl^−$ 125 mmol/liter), Voluven® (Fresenius Kabi, 6% hydroxyethyl starch (weight average molecular weight 130 000) in 0.9% sodium chloride injection), Volulyte® (Fresenius Kabi, 6% hydroxyethyl starch (weight average molecular weight 130 000) in sodium chloride intravenous infusion 0.6%, containing $Na^+$ 137 mmol, $K^+$ 4 mmol, $Mg^{2+}$ 1.5 mmol, $Cl^−$ 110 mmol, acetate 34 mmol/liter), Venofundin® (Braun, 6% hydroxyethyl starch (weight average molecular weight 130 000) in 0.9% sodium chloride injection), Tetraspan® (Braun, hydroxyethyl starch (weight average molecular weight 130 000) 6% or 10% in sodium chloride 0.625%, containing $Na^+$ 140 mmol, $K^+$ 4 mmol, $Mg^{2+}$ 1 mmol, $Cl^−$ 118 mmol, $Ca^{2+}$ 2.5 mmol, acetate 24 mmol, malate 5 mmol/liter), HAES-Steril® (Fresenius Kabi, pentastarch (weight average molecular weight 200 000) 10% in sodium chloride intravenous infusion 0.9%), Hemohes® (Braun, 6% or 10% pentastarch (weight average molecular weight 200 000), in sodium chloride intravenous infusion 0.9%), HyperHAES® (Fresenius Kabi, hydroxyethyl starch (weight average molecular weight 200 000) 6% in sodium chloride intravenous infusion 7.2%) and RescueFlow® (Vitaline, dextran 70 intravenous infusion 6% in sodium chloride intravenous infusion 7.5%).

Accordingly, in one embodiment of the invention, the resuscitation solution of the invention comprises a compound of Formula I, or a pharmaceutically acceptable salt or ester thereof, and a colloid volume expander and/or a crystalloid volume expander, wherein the colloid volume expander comprises one or more components selected from the group consisting of gelatin, succinylated gelatin, albumin, dextran, blood, and etherified starch, and wherein the crystalloid volume expander is an aqueous solution comprising at least three ions selected from the group consisting of sodium ions, chloride ions, lactate ions, potassium ions and calcium ions.

In a further embodiment of the invention there is provided a resuscitation solution comprising a compound of Formula I, or a pharmaceutically acceptable salt or ester thereof, and a colloid volume expander and/or a crystalloid volume expander, wherein the colloid volume expander comprises one or more components selected from the group consisting of gelatin, succinylated gelatin, albumin, dextran, blood, and etherified starch, and wherein the crystalloid volume expander comprises:
about 100 to 150 mmol/L of sodium ions
about 90 to 120 mmol/L of chloride ion
about 20 to 30 mmol/L of lactate
about 2 to 6 mmol/L of potassium ions
about 1 to 5 mmol/L of calcium ions.

The amount of the resuscitation solution provided to a patient can be determined by a person of skill in the art. For example, resuscitation solutions containing crystalloid volume expanders can be provided in amounts equal to between 2 and 4 times the volume lost from the patient. Resuscitation solutions containing colloid volume expanders can be provided in an amount equal to the volume lost from the patient.

The resuscitation solutions of the invention are aqueous solutions. The concentrations of each of the components can be determined by a person of skill in the art according to requirements. For example, the concentration of a compound of Formula I (or a pharmaceutically acceptable salt or ester thereof) may $10^{-6}$M to $10^{-2}$M, for example $10^{-5}$M to $3\times10^{-3}$M. In some embodiments, the compound for Formula I (or a pharmaceutically acceptable salt or ester thereof) is present at a concentration equal to or less than $10^{-2}$M. In some embodiments, the compound for Formula I (or a pharmaceutically acceptable salt or ester thereof) is present at a concentration of equal to or greater than $10^{-6}$M or $10^{-5}$M.

The resuscitation solutions of the invention may be hypotonic, hypertonic or isotonic. In some embodiments of the invention, the volume expander (and/or resuscitation or reperfusion solution) is an isotonic aqueous solution. Accordingly, the present invention also provides an isotonic aqueous solution comprising a compound for Formula I, or a pharmaceutically acceptable salt or ester thereof.

The resuscitation solutions of the invention may include additional components as deemed suitable by a person of skill in the art. For example, the resuscitation solution may also contain one or more additional components selected from the group consisting of mannitol, haemoglobin (for example in a dosage range of 2 to 9 g/liter), pegylated haemoglobin (for example MP4OX® (4 g/L PEG-Hb in lactated electrolyte solution, Sangart)), pegylated carboxyhaemoglobin (for example MP4CO® (43 mg/mL pegylated carboxyhemoglobin [≥90% CO hemoglobin saturation] in physiological acetate electrolyte solution, Sangart)), platelets (for example in a dosage of equal to or more than $50\times10^8$/liter), fibrinogen (for example in a dosage of 50 mg/kg), antifibrinolytic agents, recombinant activated coagulation factor VII (rFVIIa) and pro-thrombin complexes.

This aspect of the invention extends to the use of a compound for Formula I, or a pharmaceutically acceptable salt or ester thereof, volume expander, and optionally additional components (such as those listed above) in the manufacture of a resuscitation solution.

Treatment of trauma haemorrhage may be tailored according to the patient's requirements. Example treatment regimens are discussed in Rossaint et al. (2010), *Critical Care*, 14:R52.

When preparing aqueous resuscitation solutions comprising a compound of Formula I, a person of skill in the art may take any necessary steps to increase the solubility of the compounds of Formula I, as discussed above.

A compound of Formula I, or a pharmaceutically acceptable salt or ester thereof, may be added to donor blood prior to transfusion to reduce organ damage caused by the haemorrhage. Therefore, in a further aspect of the invention there is provided a sample or unit of isolated blood comprising a compound of Formula I, or a pharmaceutically acceptable salt or ester thereof. The sample or unit of isolated blood is for transfusion in a patient suffering from trauma haemorrhage or an associated condition.

The unit of isolated blood for transfusion might not contain a whole blood sample, but generally comprises red blood cells, plasma and platelets. The unit of isolated blood may further comprise white blood cells and/or clotting factors (such as factor V or factor VIII). The unit of blood is generally provided in a unit dosage form, for example an amount of 300 to 700 ml, suitably 400 to 600 ml. The blood may be obtained from a human donor patient and may be stored prior to administration to the patients suffering trauma haemorrhage.

The type of blood to be administered to a patient will be determined by the skilled person. For example, the blood may be type A, type B, type AB or type 0, according to the patient's requirements. The blood may be rhesus positive or negative, according to the patient's requirements.

The concentration of the compound of Formula I (or a pharmaceutically acceptable salt or ester thereof) in the unit of isolated blood may be $10^{-6}$M to $10^{-2}$M, for example $10^{-5}$M to $3\times10^{-3}$M. In some embodiments, the compound for Formula I (or a pharmaceutically acceptable salt or ester thereof) is present at a concentration equal to or less than $10^{-2}$M. In some embodiments, the compound for Formula I (or a pharmaceutically acceptable salt or ester thereof) is present at a concentration of equal to or greater than $10^{-6}$M or $10^{-5}$M.

In a further aspect of the invention there is provided a method of treating trauma haemorrhage, trauma haemorrhage-induced organ injury, trauma haemorrhage-induced multiple organ failure, stroke or burns injury, comprising administering a compound of Formula I, or a pharmaceutically acceptable salt or ester thereof, a pharmaceutical composition of the invention, a resuscitation solution of the invention, or a unit of isolated blood for transfusion of the invention, to a patent in need thereof.

The compound, pharmaceutical composition, resuscitation solution or unit of blood may be administered to a patient after suffering trauma haemorrhage. Alternatively, or additionally, it may be administered prior to surgery to avoid post-surgical complications such as organ damage due to blood loss. Routes of administration can be any suitable route known to a person of skill in the art, for example oral (including buccal or sublingual), parenteral, intravenous, intramuscular, intrathecal or intraperitoneal administration, or administration by inhalation. The unit of isolated blood for transfusion of the invention is generally administered intravenously after suffering trauma haemorrhage.

In one embodiment of the invention, there is provided artesunate for use in the treatment of trauma haemorrhage. The artesunate is administered to patients suffering from blood loss to minimise organ damage. The solution can be administered intravenously at a dose in the range of 0.1 mg/kg to 10 mg/kg. The solution may be administered as an aqueous resuscitation solution comprising a colloid or crystalloid volume expander.

As noted above, the inventors have also surprisingly found that administration of artesunate and its related compounds can reduce the infarct size in MI and can even reduce the level of damage after the infarction has taken place. Accordingly, in a further aspect of the invention, there is provided a compound according to Formula I, or a pharmaceutically acceptable salt or ester thereof, for use in the treatment of myocardial infarction or coronary heart disease or a disorder associated with myocardial infarction or coronary heart disease.

"Myocardial infarction" as used herein includes transmural MI and subendocardial MI. Transmural MI is associated with atherosclerosis involving a major coronary artery. Subendocardial MI involves a small area in the subendocardial wall of the left ventrical, ventricular septum, or papillary muscles. Aspects of the invention also extend to the treatment of coronary heart disease and conditions associated with myocardial infarction and/or coronary heart disease, including cardiac arrest (effectively whole-body ischaemia) and organ damage caused by cardiac arrest.

Diseases associated with ischaemia-reperfusion include ischaemia-reperfusion-induced pancreatitis, acute lung injury (discussed above), adult respiratory distress syndrome (ARDS, also discussed above), angina pectoris and pulmonary hypertension.

Pulmonary hypertension refers to an increase in blood pressure in the pulmonary artery, pulmonary vein or pulmonary capillaries (together known as the lung vasculature). "Primary" or "essential" pulmonary hypertension refers to the fact that there is no single identifiable cause, although environmental and/or genetic risk factors may be present.

The World Health Organisation has classified pulmonary hypertension into 5 groups, I to V. WHO Group I is pulmonary arterial hypertension (PAH) and includes, idiopathic PAH, familial PAH, PAH associated with other diseases (such as collagen vascular disease (e.g. scleroderma), congenital shunts between the systemic and pulmonary circulation, portal hypertension, HIV infection, drugs, toxins, or other diseases or disorders) and PAH associated with venous or capillary disease.

WHO Group II is pulmonary venous hypertension associated with left heart disease, such as atrial or ventricular disease or valvular disease (e.g. mitral stenosis). WHO Group III is pulmonary hypertension associated with lung diseases and/or hypoxemia, such as chronic obstructive pulmonary disease (COPD) and interstitial lung disease (ILD). WHO Group IV is pulmonary hypertension due to chronic thrombotic and/or embolic disease, such as pulmonary embolism in the proximal or distal pulmonary arteries. WHO Group V is pulmonary hypertension associated with miscellaneous disorders.

Angina pectoris, also known simply as angina, is chest pain due to ischaemia of the heart muscle. This is generally due to obstruction of the coronary arteries or due to spasm resulting in a restriction of blood flow to the heart. Coronary heart disease is the main cause of angina due to atherosclerosis of the cardiac arteries. "Angina" as used herein is intended to include stable angina, unstable angina and microvascular angina.

Pulmonary arterial hypertension (PAH) is a syndrome characterised by a progressive increase in pulmonary vascular resistance leading to right ventricular overload and eventually to right ventricular failure and premature death.

The increase in pulmonary vascular resistance is related to a number of progressive changes in the pulmonary arterioles, including vasoconstriction, obstructive remodelling of the pulmonary vessel wall through proliferation in the various layers of the blood vessel wall (smooth muscle cell and endothelial cell proliferation), inflammation and in-situ thrombosis.

The main histological features include medial hypertrophy, intimal thickening, adventitial thickening, plexiform lesions and in-situ thrombosis. The plexiform lesion represents a focal proliferation of endothelial and smooth muscle cells and is pathognomonic of PAH. PAH may be defined as a sustained elevation of mean pulmonary arterial pressure to more than 25 mmHg at rest or to more than 30 mmHg while exercising, with a normal pulmonary wedge pressure (<15 mmHg). In most cases the earliest symptom is dyspnoea on physical exertion. Other symptoms include syncope or near syncope, fatigue and peripheral oedema. Chest tightness and pain similar to angina may occur, particularly on physical exertion.

The compounds of the first aspect of the invention are also useful in surgical procedures that result in ischaemia-reperfusion of the whole or part of the heart, including heart transplantation or heart and lung transplantation, in particular for the perfusion of a heart during transplantation to reduce any damage caused in ischaemia. Similarly, the compounds of the first aspect of the invention are also useful in coronary artery bypass surgery, in particular for the perfusion of arteries or veins during the procedure, or during procedures to stent a coronary artery, for example with a balloon. A compound of the first aspect of the invention may be administered to patients undergoing coronary surgery, such as heart transplantation or coronary artery bypass surgery, to minimise any damage caused by ischaemia and ischaemia-reperfusion. The compounds of the first aspect of the invention are also useful in the treatment of pulmonary hypertension.

In embodiments of the invention, the compound of Formula I, or salts or derivatives thereof, may be administered in combination with one or more pharmaceutically active agents. In particular, when treating MI myocardial infarction or coronary heart disease or a disorder associated with myocardial infarction or coronary heart disease (including cardiac arrest), a compound of the invention may be for administration in combination with one or more pharmaceutically active compounds selected from the group consisting of an HMG-CoA reductase inhibitor, erythropoietin (EPO) or an analogue thereof, a PPAR (peroxisome proliferator-activated receptors)-gamma ligand, a PPAR-beta ligand, a PPAR-alpha ligand a nitrate-containing compound, a nitric oxide (NO)-donor, a phenylpropanoid, a glycogen synthase kinase 3 inhibitor, andrographolide or analogues thereof, an antioxidant, a vitamin D receptor (VDR) modulator (VDRM), a lipoxin, annexin A1 (AnxA1) or analogues thereof, pentoxyphylline, a histone deacetylase (HDAC) inhibitor, carbenoxolone, glycyrrhizin, high-mobility group protein B1 (HMGB1) and analogues thereof, an HMGB1 inhibitor, activated protein C, salicylic acid or derivatives thereof, a prostacyclin or derivative thereof, a lipid-rich solution, a CXCR2 modulator and a phosphodiesterase inhibitor.

The HMG-CoA reductase inhibitors may be for administration in the dosage range of 0.03-10 mg/kg). The HMG-CoA reductase inhibitor may be a statin, for example a statin selected from the group consisting of simvastatin, atorvastatin, pravastatin, cerivastatin, fluvastatin, lovastatin, mevastatin, pitavastatin and rosuvastatin.

Erythropoietin (EPO) may be for administration in the dosage range of 1000 IU/kg). The erythropoietin analogue may be ARA-290 (Araim Pharmaceuticals, Ossining, N.Y., USA, for example in the dosage range of 0.03-10 ng/kg). ARA 290 is an 11-amino acid peptide with a protected N-terminus (by the 5-membered ring structure of pyroglutamic acid) and a free carboxyl group at the C-terminus. All amino acid residues are in the L-configuration. The amino acid sequence (in the N- to C-terminal direction) is Pyr-Glu-Gln-Leu-Glu-Arg-Ala-Leu-Asn-Ser-Ser-OH, where Pyr represents pyroglutamic acid. An EPO derivative may also be used, for example PEGylated EPO or carbamylated EPO.

The PPAR (peroxisome proliferator-activated receptors)-gamma ligand may be rosiglitazone, pioglitazone, ciglitazone, prostaglandin A1 or prostaglandin D2 (for example in the dosage range of 0.03-10 mg/kg) or 15-deoxyDelta12, 14-prostaglandin $J_2$ (15D-PGJ$_2$, for example at a dosage range of 0.1-3 mg/kg provided intravenously). The PPAR-beta ligand may be GW0742 (Sigma) or GW501516 (for example in the dosage range 0.001 to 3 mg/kg). The PPAR-alpha ligand may be fenofibrate, clofibrate or WY 14643 (discussed in Wayman et al. (2002), FASEB J, 16(9):1027-40.

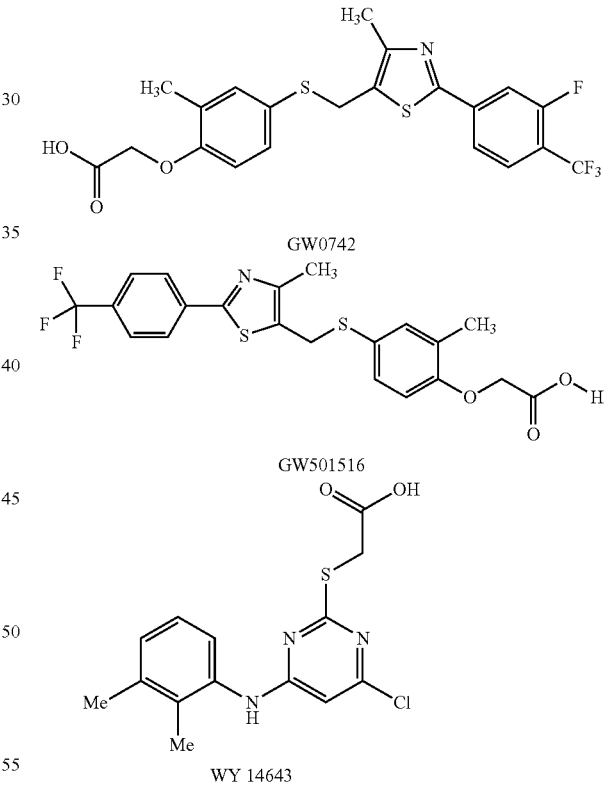

The nitrate-containing compound may be sodium nitrate, lithium nitrate, potassium nitrate, nitric acid, magnesium nitrate, calcium nitrate. The nitrate-containing compound may also be an organic nitrate, such as glyceryl trinitrate (GTN). The nitric oxide (NO)-donor may be diazeniumdiolate.

The phenylpropanoid can be coumarin, osthole (for example up to 100 mg/kg per dose) or Meriva® (curcumin complexed with phosphatidylcholine, available from Thorne Research, Dover, Id., USA). Lipid-rich solutions comprising phosphatidylcholine and/or high-density lipoprotein (HDL) and/or sphingosylphosphorylcholine (SPC, discussed in Murch et al (2008), Crit Care Med, 36(2):550-9) may also be used (or any of these components individually). Lipoproteins are generally defined as "high density" if their density is greater than or equal to 1.063 g/ml. HDLs may have a diameter of 5 to 15 nm. HDLs may comprise 30% or more of protein.

The glycogen synthase kinase 3 inhibitor can be lithium (for example in the dosage range of 0.1-30 mg/kg) or TDZD-8 (Sigma-Aldrich, for example in the dosage range of 0.03-10 mg/kg), NP-12 (Sigma-Aldrich, for example in the dosage range of 0.03-10 mg/kg) or valproate (a salt of valproic acid, for example in the dosage range of 0.03-10 mg/kg).

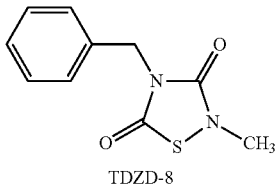

TDZD-8

Andrographolide may be for administration in the dosage range of 0.1 to 3 mg/kg.

The antioxidant may be superoxide dismutase, tempol (spin trap agent, for example in the dosage range of 1-100 mg/kg), Trolox® (Hoffman-LaRoche, for example in the dosage range of 1-100 mg/kg) or resveretrol and analogues thereof, such as RSVA314 and RSVA405 (discussed in Vingtdeux et al. (2011), FASEB J, 25(1):219-231).

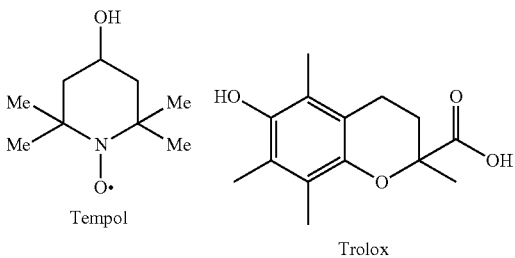

Tempol

Trolox

The vitamin D receptor (VDR) modulator (VDRM) may be, vitamin D, calcitriol, paricalcitol, doxercalciferol or VS-105 (Vidasym, Chicago, Ill., USA).

The lipoxin may be lipoxin $A_4$. The Annexin A1 analogue may be a ligand of the formyl peptide receptor type 2 (FPR2/ALX) such as, antiflammin-2, fMLF or Ac2-26 (N-terminal acyl), AC1-25, UDP25 (Unigene) and UDP26 (Unigene).

Ac-Ala-Met-Val-Ser-Glu-Phe-Leu-Lys-Gln-Ala-Trp-Phe-Ile-Glu-Asn-Glu-Glu-Gln-Glu-Tyr-Val-Gln-Thr-Val-Lys Ac2-26

Pentoxyphylline may be for administration in the dosage range of 0.1 to 400 mg/kg). Carbenoxolone may be for administration in the dosage range of 0.01-30 mg/kg. Glycyrrhizin, a major active constituent of liquorice root (*Glycyrrhiza glabra*) may be for administration in the dosage range of 0.1-30 mg/kg. The histone deacetylase (HDAC) inhibitor may be KAR3166 (Karus, Southampton, UK), KAR3000 (Karus, Southampton, UK) or romidepsin (also known as NSC 630176, Istodax®, depsipeptide, FR901228 and FK288)

The high-mobility group protein B1 (HMGB1) analogues may be recombinant C-terminal domain and A-box of HMGB1 (discussed in Banerjee & Kundu, Nucleic Acids Res (2003), 31(12):3236-47 and Andersson & Tracey, Annu Rev Immunol (2011), 29:139-62), or peptides derivatives thereof. The HMGB1 inhibitor may be an anti-HMB 1 antibody. The salicylic acid derivative may be a salicylic salt (such as sodium salicylate), for example in the dosage range of up to 100 mg/kg or aspirin (for example in the dosage range of up to 300 mg/kg).

Prostacyclin analogues may be iloprost (Bayer Schering) or cicaprost (Cayman chemical). Phosphodiesterase (PDE) inhibitors include sildenafil (Viagra®) or tadalafil (Cialis®), for example at a dosage of 0.1 mg/kg to 10 mg/kg (discussed in Sim et al. (2011), Int J Cardiol, 146(3):459-60 and Koka & Kukreja (2010), Mol Cell Pharmacol., 2(5):173-178). The PDE inhibitors may be type 1, 2, 3, 4 or 5 PDE selective inhibitors, or non-selective PDE inhibitors.

CXCR2 is also known as "interleukin 8 receptor, beta", or ILRB8. The CXCR2 modulators may be activators or inhibitors of CXCR2. Antagonists of CSCR2 are discussed in US 2009/0258906. CXCR2 modulators are also discussed in Kim et al. (2011), Am J Respir Crit Care Med (published ahead of print, 21 Apr. 2011) and Kapoor & Thiemermann (2011), Am J Respir Crit Care Med, 183(2):150-1.

A compound of Formula I, or a pharmaceutically acceptable salt or ester thereof, may also be for administration in combination with stem cells, such as mesenchymal stem cells, embryonic stem cells, endothelial progenitor cells, cardiac stem cells or induced pluripotent stem cells. The stem cells may be administered in a dosage of 10,000 to 10 million cells per administration. Alternatively, a compound of Formula I, or a pharmaceutically acceptable salt or ester thereof, may also be for administration in combination with the supernatant of such cells collected after up to 24 hours incubation ex vivo in the absence of presence of a compound of Formula I and/or EPO.

A compound of Formula I, or a pharmaceutically acceptable salt or ester thereof, may also be for administration in combination with the flavonoid-rich fraction of *Coreopsis tinctoria* containing marein (discussed in Dias et al., J. Ethnopharmacol (2010), 132(2):483-90). This may be for administration in the dosage range of 0.1-30 mg/kg for marein and up to 300 mg/kg for the fraction.

A compound of Formula I, or a pharmaceutically acceptable salt or ester thereof, may also be administered with conventional MI therapy, for example those described in Wakai (2011), Clin Evid (Online), pii:0202 and Jernberg et al. (2011), JAMA, 305(16):1677-84.

Pharmaceutical compositions of the invention therefore may include one or more further pharmaceutically active agents. Example additional pharmaceutical compositions include those listed as useful for the first aspect of the invention for administration in combination with a compound of the invention. The invention therefore also provides a pharmaceutical composition comprising a compound of Formula I, or a pharmaceutically acceptable salt or ester thereof, and one or more additional components selected from the group consisting of an HMG-CoA reductase inhibitor, erythropoietin or an analogue thereof, a PPAR (peroxisome proliferator-activated receptors)-gamma ligand, a PPAR-beta ligand, a nitrate-containing compound, a nitric oxide (NO)-donor, a phenylpropanoid, a glycogen synthase kinase 3 inhibitor, andrographolide or analogues thereof, an antioxidant, a vitamin D receptor (VDR) modulator (VDRM), a lipoxin, annexin A1 (AnxA1) or analogues thereof, pentoxyphylline, a histone deacetylase (HDAC)

inhibitor, carbenoxolone, glycyrrhizin, high-mobility group protein B1 (HMGB1) and analogues thereof, an HMGB1 inhibitor and activated protein C.

In a further aspect of the invention there is provided a pharmaceutical composition comprising a compound of Formula I, or salts or derivatives thereof, and a pharmaceutically acceptable excipient for use in the treatment of myocardial infarction or coronary heart disease or a disorder associated with myocardial infarction or coronary heart disease.

Dosages of the pharmaceutical compositions of the present invention can vary between wide limits, depending upon the disease or disorder to be treated, the age and condition of the individual to be treated, etc. and a physician will ultimately determine appropriate dosages to be used. However, the present inventors have discovered that for myocardial infarction, coronary heart disease and related disorders in particular, such disorders can be treated using low concentrations of the compounds that avoid the adverse side effects usually associated with artemisinin and derivatives thereof, such as electrolyte disturbances, abdominal pain, anorexia, diarrhoea, vomiting, nausea, palpitation, prolonged QT interval, cough, headache, dizziness, sleep disturbances, asthenia, paraesthesia, arthralgia, myalgia, pruritus, rash, ataxia, hypoaesthesia, and clonus.

For example, a compound of Formula I, or a pharmaceutically acceptable salt or ester thereof, may be administered in an amount of 0.1 to 50 mg/kg, or 0.1 to 30 mg/kg, or between 0.1 and 3 mg/kg, or between 0.3 and 3 mg/kg. In some embodiments, the artesunate is administered in amount equal to or less than 50, 30, 25, 20, 15, 10, 5 or 1 mg/kg. The compound of Formula I, or a pharmaceutically acceptable salt or ester thereof, may be administered at these dosages only once. Alternatively, a compound of Formula I, or a pharmaceutically acceptable salt or ester thereof, may be administered at these dosages once per day, twice per day, three times per day, four times per day five times per day, wherein preferably each bolus is less than the dosages specified above (rather than a cumulative dosage for the whole day). In some embodiments, the compounds are administered no more that three times per day, or no more than two times per day, or only once per day. In some embodiments, the dosages are given at least 6 hours apart, preferably at least 12 hours apart. The compounds may be administered as a bolus or alternatively may be administered over a period of time as deemed suitable by a skilled person, for example by intravenous drip. In some embodiments, the compounds of Formula I, or pharmaceutically acceptable salts or esters thereof, may be administered in an amount of between 0.1 and 5 mg/kg (or between 0.1 and 3 mg/kg) as a single bolus dose, or once per day, or twice per day, or three times per day, or more.

In a further aspect of the invention there is provided the use of a compound of Formula I, or a pharmaceutically acceptable salt or ester thereof, in the manufacture of a medicament for the treatment of myocardial infarction or coronary heart disease or a disorder associated with myocardial infarction or coronary heart disease. In another aspect of the invention there is provided the use of artemisinin and derivatives thereof, or a pharmaceutically acceptable salt or ester thereof, for use in the manufacture of a medicament for the treatment of myocardial infarction or coronary heart disease or a disorder associated with myocardial infarction or coronary heart disease. In one embodiment, the artemisinin derivatives are selected from the group consisting of artesunate, artemether, dihydroartemisinin, artelinic acid and artemotil.

In a further aspect of the invention there is provided a kit of parts comprising a compound of Formula I, or a pharmaceutically acceptable salt or ester thereof, and one or more further pharmaceutically active agent for simultaneous, separate or sequential administration. The kit of parts may optionally include instructions for use. The compound of Formula I may be present in a unit-dosage form. The one or more further pharmaceutically active agents may include any of those components listed as being useful for combinatorial therapy of myocardial infarction or coronary heart disease or a disorder associated with myocardial infarction or coronary heart disease described above.

As noted above, in another aspect of the invention, there is provided a reperfusion solution comprising a compound of Formula I, or a pharmaceutically acceptable salt or ester thereof, and one or more volume expanders. This aspect of the invention extends to the use of a compound of Formula I, or a pharmaceutically acceptable salt or ester thereof, in the manufacture of a reperfusion solution. The reperfusion solutions of the invention are essentially identical to the resuscitation solutions of the invention described above. Therefore, all of the preferred and optional components of the resuscitation solutions of the invention apply equally to the reperfusion solutions of the invention (for example, the specific volume expanders, the presence of particular ions and other components, as well as the preferred concentration ranges noted above).

In a further aspect of the invention, there is provided an aqueous composition comprising a compound of Formula I, or a pharmaceutically acceptable salt or ester thereof, and sodium bicarbonate. The sodium bicarbonate may be present at a concentration of between 5% and 15% by weight, for example between 5% and 10% by weight or between 7% and 10% by weight. In some embodiment the sodium bicarbonate is present in an amount of equal to or more than 1%, 2%, 3%, 4%, 5%, 6%, 7% or 8% by weight.

The sodium and bicarbonate ions in the aqueous composition of the invention may each be present in a concentration of about 500 mM/L to about 1500 mM/L, for example about 750 mM/L to about 1250 mM/L, or about 800 mM/L to 1200 mM/L, or about 900 mM/L to about 1100 mM/L. In some embodiments of the invention, the sodium and bicarbonate ions in the composition of the invention may each be present in a concentration of equal to or less than about 500, 600, 700, 800, 900, 950 or 1000 mM/L.

Such aqueous compositions of the invention are useful for correcting metabolic acidosis in a patient suffering from myocardial infarction, or in a patient that has recently suffered a myocardial infarction. This aspect of the invention therefore extends to a compound of Formula I, or a pharmaceutically acceptable salt or ester thereof, or an aqueous composition of the invention, for use in the treatment of acidosis. This aspect of the invention also extends to the use of a compound of Formula I, or a pharmaceutically acceptable salt or ester thereof, and sodium bicarbonate in the manufacture of a medicament for the treatment of acidosis, and corresponding methods of treatment. The aqueous compositions of the invention may also be useful in the treatment of coronary heart disease or myocardial infarction and their related conditions.

In another aspect of the invention there is provided a method of treating myocardial infarction or coronary heart disease (or its related disorders), comprising administering a compound of Formula I, or a pharmaceutically acceptable salt or ester thereof, a pharmaceutical composition of the invention, a reperfusion solution of the invention, or an aqueous composition of the invention, to a patent in need thereof.

The compound, pharmaceutical composition, reperfusion solution or aqueous composition may be administered to a patient after suffering myocardial infarction or whilst suffering from a myocardial infarction. Alternatively, it may be administered prior to heart transplant surgery or coronary bypass surgery to avoid post-surgical complications such as ischaemia due to a restriction of blood flow.

Routes of administration can be any suitable route known to a person of skill in the art, for example oral (including buccal or sublingual), topical, parenteral, intravenous, intramuscular, intrathecal or intraperitoneal administration, or administration by inhalation.

In a still further aspect of the invention, there is provided a method of perfusing a coronary tissue, vein, artery, heart, lung, heart valve or a combination thereof comprising bathing the coronary tissue, vein, artery, heart, lung or heart valve or combination thereof in the reperfusion solution of the invention. The heart or tissue is obtained from a deceased donor patient (either a live patient or a cadaver). In some embodiments, the donor patient may be an animal, such as a pig (for example in the xenotransplantation of porcine heart valves), and therefore this embodiment of the invention extends to a method of perfusing a heart valve, comprising bathing the heart valve in the reperfusion solution of the invention. In some embodiments, the organ or part of the organ may have been created in vitro using tissue engineering.

In another aspect of the invention, there is provided a method of heart transplantation (or heart and lung transplantation), comprising implanting heart that has been perfused according to the method of perfusion of the invention into a patient in need thereof (a recipient patient).

In another aspect of the invention, there is provided a method of coronary artery bypass, comprising implanting a vein or artery that has been perfused according to the method of perfusion of the invention into a patient in need thereof (a recipient patient).

In another a further aspect of the invention, there is provided a method of heart valve transplantation, comprising implanting a heart valve that has been perfused according to the method of perfusion of the invention into a patient in need thereof (a recipient patient).

In another aspect of the invention, there is provided a method of implanting a coronary stent, comprising administering a compound of Formula I, or a pharmaceutically acceptable salt or ester thereof, to a patient before, during or after stent implantation. The coronary stent may be a drug-eluting stent.

In some embodiments, the donor patient and the recipient patient are different patients (allotransplantation). However, they may be the same patient (autologous transplantation or autotransplantation), for example in the case of coronary artery bypass surgery where arteries or veins from one part of a patient's body is transplanted to the coronary vasculature. The donor patient may be of a different species (for example in the case of xenotransplantation of heart valves).

Organs or parts of organs or tissues that may be transplanted or perfused generally include arteries, veins, hearts, lungs, heart valves and combinations thereof.

In one embodiment of the invention, there is provided artesunate for use in the treatment of myocardial infarction. The artesunate is as an intravenous preparation administered to patients suffering from myocardial infarction, or patients that have recently suffered a myocardial infarction, to reduce the size of the infarct and the damage to the myocardium. The solution can be administered intravenously at a dose in the range of 0.1 mg/kg to 10 mg/kg. The solution may be administered as an aqueous reperfusion solution comprising a colloid or crystalloid volume expander, or as an aqueous composition comprising a compound of Formula I and sodium bicarbonate.

Features of the first aspect of the invention apply to the second and subsequent aspects of the invention, mutatis mutandis.

The invention will now be described with reference to the following Examples, which are presented for the purposes of reference only and are not intended to be limiting on the scope of the invention. In the Examples, references are made to a number of Figures, in which:

FIG. 1 shows alterations in MAP in rats subjected to (i) surgical procedure alone (Sham, n=4), or surgical procedure and haemorrhagic shock then treated with (ii) vehicle (10% DMSO, 1 ml/kg i.v., HS Control, n=10) or (iii) artesunate (1, 3 or 10 mg/kg i.v., HS+Artesunate 1 mg/kg; n=6, HS+Artesunate 3 mg/kg; n=7 and HS+Artesunate 10 mg/kg; n=8, respectively) on resuscitation. Data is expressed as mean±SEM. * $P<0.05$ sham vs. HS Control.

FIG. 2 shows alterations in serum levels of (a) urea and (b) creatinine; and (c) creatinine clearance, in rats subjected to (i) surgical procedure alone (Sham, n=4), or surgical procedure and haemorrhagic shock then treated with (ii) vehicle (10% DMSO, 1 ml/kg i.v., HS Control, n=10) or (iii) artesunate (1, 3 or 10 mg/kg i.v., HS+Artesunate 1 mg/kg; n=6, HS+Artesunate 3 mg/kg; n=7 and HS+Artesunate 10 mg/kg; n=8, respectively) on resuscitation. Data is expressed as mean±SEM. * $P<0.05$ vs. HS Control.

FIG. 3 shows alterations in serum levels of (a) AST, (b) ALT and (c) CK in rats subjected to (i) surgical procedure alone (Sham, n=4), or surgical procedure and haemorrhagic shock then treated with (ii) vehicle (10% DMSO, 1 ml/kg i.v., HS Control, n=10) or (iii) artesunate (1, 3 or 10 mg/kg i.v., HS+Artesunate 1 mg/kg; n=6, HS+Artesunate 3 mg/kg; n=7 and HS+Artesunate 10 mg/kg; n=8, respectively) on resuscitation. Data is expressed as mean±SEM. * $P<0.05$ vs. HS Control.

Figure 6:
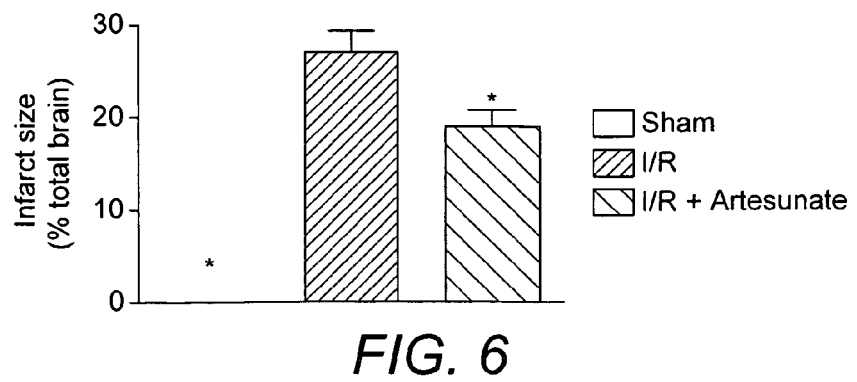

FIG. 6 Alterations in infarct size in rats subjected to surgical procedure alone and treated with vehicle (Sham, n=4); or subjected to cerebral ischaemia and reperfusion and treated with vehicle (I/R, n=7) or with 3 mg/kg artesunate (FR+Artesunate, n=7) on reperfusion and 6 h after the onset of reperfusion. Data is expressed as mean±SEM. * $P<0.05$ vs. I/R.

Figure 7:
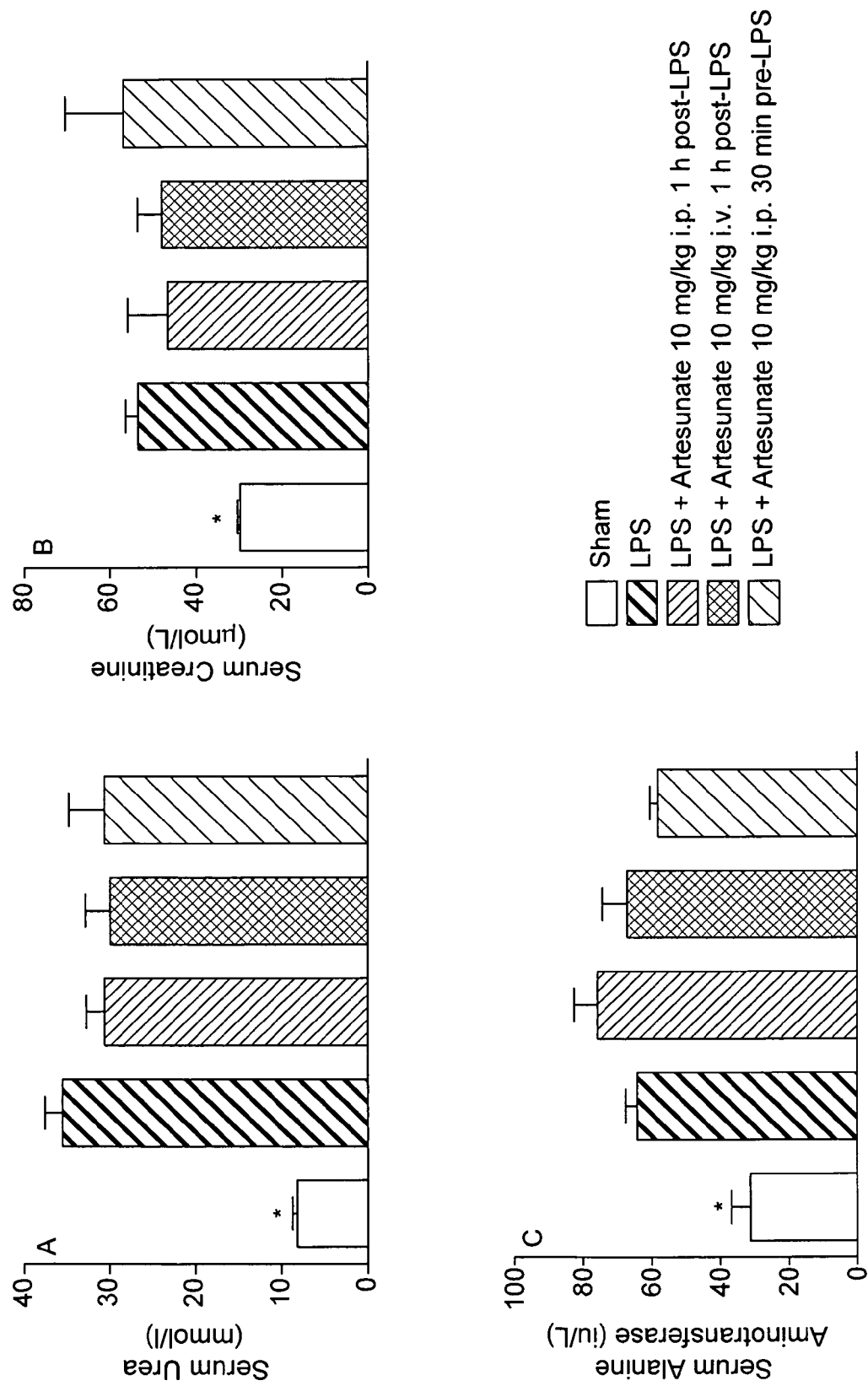

FIG. 7 Alterations in serum levels of (a) urea and (b) creatinine, and (c) ALT, in mice subjected to (i) sham-operation (Sham, n=5), or septic shock then treated with (ii) vehicle (10% DMSO, 1 ml/kg i.v., LPS, n=10) or (iii) artesunate (10 mg/kg, LPS+Artesunate 10 mg/kg i.p. 1 h post-LPS, n=6, LPS+Artesunate 10 mg/kg i.v. 1 h post-LPS, n=3, LPS+Artesunate 10 mg/kg i.p. 30 min pre-LPS, n=2. Data is expressed as mean±SEM. * P<0.05 vs. LPS.

Figure 8:
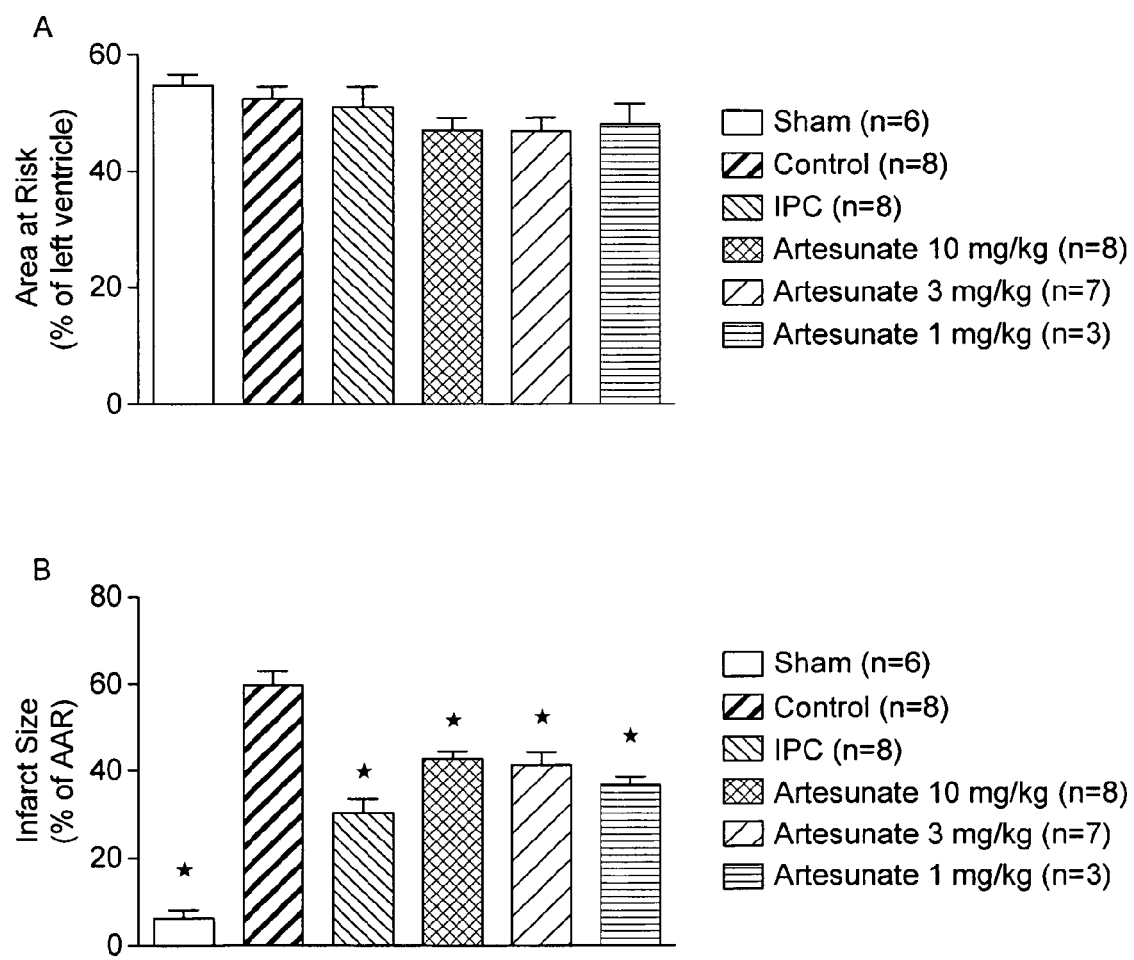

FIG. 8 shows (A) area at risk and (B) infarct size of rats subjected to surgical procedure alone and treated with vehicle (Sham, 10% DMSO 1 ml/kg i.v., n=6), or regional myocardial ischaemia (25 min) and reperfusion (2 h) and treated with vehicle (Control, 10% DMSO 1 ml/kg i.v., n=8), or 2 cycles of IPC (5 min) followed by LAD-occlusion (25 min) and reperfusion (2 h) and treated with vehicle (IPC, 10% DMSO 1 ml/kg i.v., n=8), or regional myocardial ischaemia (25 min) and reperfusion (2 h) and treated with Artesunate (Artesunate, 10% DMSO, 1, 3 or 10 mg/ml at 1 ml/kg i.v., n=8). ★P<0.05 vs. Control.

Figure 9:
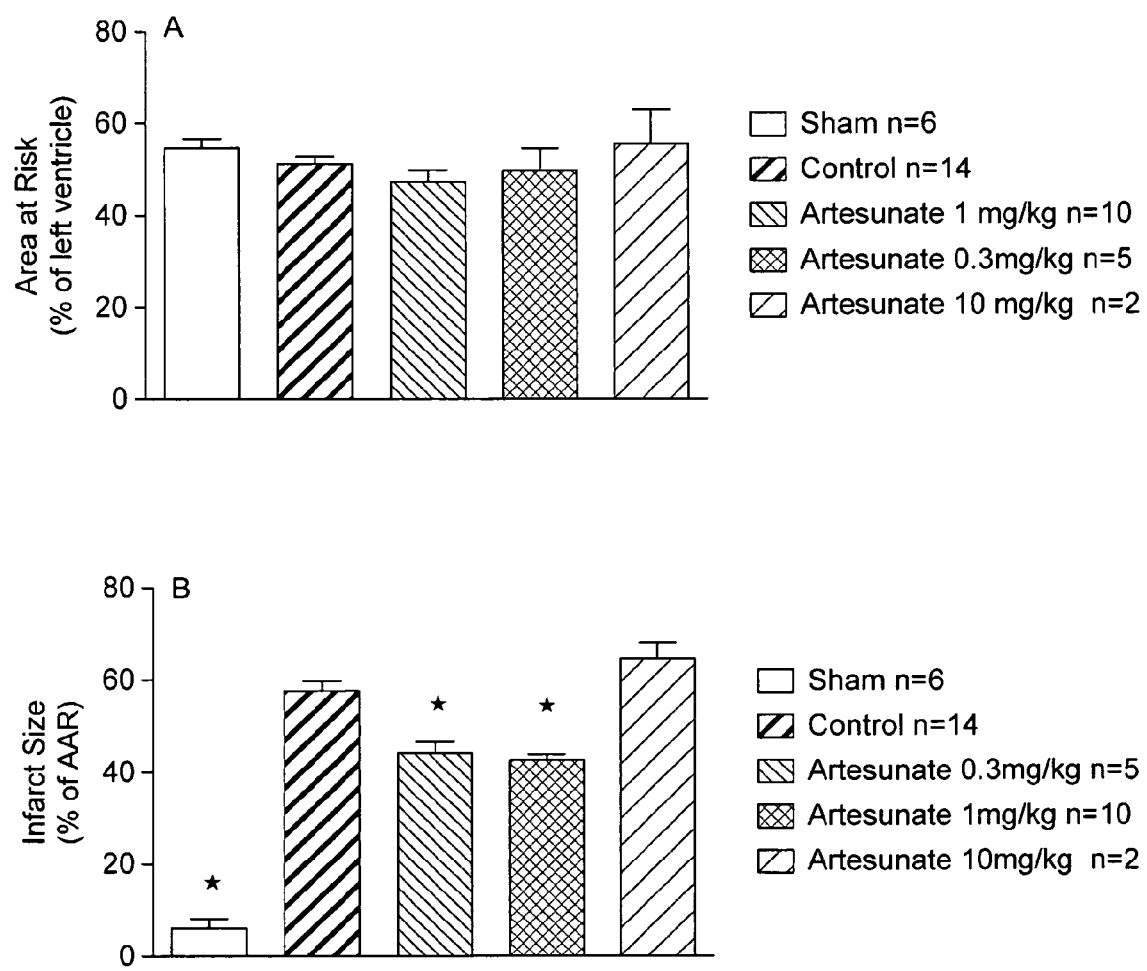

FIG. 9 shows (A) area at risk and (B) infarct size of rats subjected to surgical procedure alone and treated with vehicle (Sham, 5% sodium bicarbonate 1 ml/kg i.v., n=6), or regional myocardial ischaemia (25 min) and reperfusion (2 h) and treated with vehicle (Control, 5% sodium bicarbonate 1 ml/kg i.v., n=14), or regional myocardial ischaemia (25 min) and reperfusion (2 h) and treated with artesunate (0.3, 1 or 10 mg/kg i.v., n=2-10). ★P<0.05 vs. Control.

Figure 10:
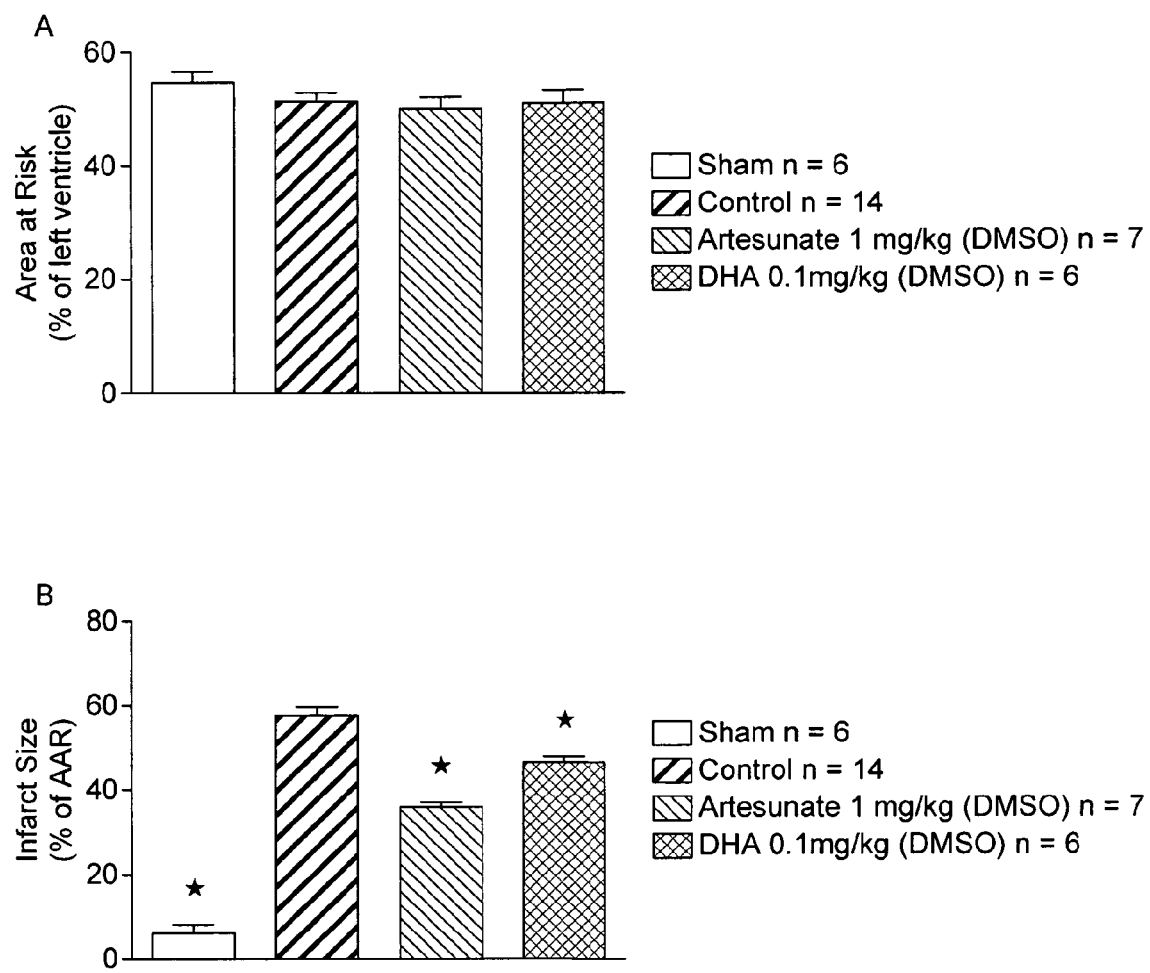

FIG. 10 shows (A) area at risk and (B) infarct size of rats subjected to surgical procedure alone and treated with vehicle (Sham, 10% DMSO 1 ml/kg i.v., n=6), or regional myocardial ischaemia (25 min) and reperfusion (2 h) and treated with vehicle (Control, 10% DMSO 1 ml/kg i.v., n=14), or regional myocardial ischaemia (25 min) and reperfusion (2 h) and treated with artesunate (1 mg/kg i.v., n=7), or regional myocardial ischaemia (25 min) and reperfusion (2 h) and treated with dihydroartemisnin (DHA 0.1 mg/kg i.v., n=6). ★P<0.05 vs. Control.

EXAMPLES

The animal protocols followed in this study were approved by the local Animal Use and Care Committee in accordance with the derivatives of both the Home Office Guidance on the Operation of Animals (Scientific Procedures) Act 1986 published by Her Majesty's Stationary Office and the Guide for the Care and Use of Laboratory Animals of the National Research Council. Statistical analysis was generally carried out using GraphPad Prism 5.03 (GraphPad Software, San Diego, Calif., USA) and a P value of less than 0.05 was considered to be significant. All values described in the text and figures are expressed as mean±standard error of the mean (SEM) for n observations.

1. Evaluation of the Effects of Artesunate on the Organ Injury and Dysfunction Induced by Trauma Haemorrhage in the Rat 1.1 Surgical Procedure Thirty-five male Wistar rats (271±5 g) were anaesthetised with sodium thiopentone (120 mg/kg i.p., LINK Pharmaceuticals Ltd., West Sussex, UK) and anaesthesia was maintained by supplementary injections (−10 mg/kg i.v.) of sodium thiopentone as and when required. The animals were placed onto a thermostatically controlled heating mat (Harvard Apparatus Ltd., Kent, UK) and body temperature was maintained at 37±1° C. by means of a rectal probe attached to a homeothermic blanket. A tracheotomy was performed by inserting into the lumen of the trachea a small length of polyethylene tubing [Internal Diameter (ID) 1.67 mm, Portex, Kent, UK] to maintain airway patency and facilitate spontaneous respiration. The left femoral artery was cannulated (ID 0.40 mm, Portex) and connected to a pressure transducer (SP844 blood pressure sensor, Memscap, U.S.A.) for the measurement of mean arterial blood pressure (MAP) and derivation of heart rate (HR) from the pulse waveform, which were both displayed on a data acquisition system (Powerlab 8SP, Chart v5.5.3, AD Instruments, Hastings, U.K.) installed on an Intel-based computer running Windows XP for the duration of the experiment.

The right carotid artery was cannulated (ID 0.58 mm, Portex) to facilitate the withdrawal of blood using a heparinised syringe. The right jugular vein was cannulated (ID 0.40 mm, Portex) for the administration of Ringer's Lactate (RL), shed blood, test compounds and/or vehicle. The bladder was also cannulated (ID 0.76 mm, Portex) for the collection of urine. Upon completion of the surgical procedure, cardiovascular parameters were allowed to stabilise for a period of 15 min.

1.2 Haemorrhage and Resuscitation

After the stabilisation period, blood was withdrawn via the cannula inserted in the right carotid artery in order to achieve a fall in MAP to 35±5 mmHg within 10 min From this point onwards, MAP was maintained at 35±5 mmHg for a period of 90 min either by further withdrawal of blood during the compensation phase (MAP rises following blood withdrawal due to sympathetic response) or administration of Ringer's Lactate i.v. during the decompensation phase (animals are unable to increase and maintain high MAP). The average volume of blood withdrawn during haemorrhage was 9.8±0.2 ml (n=31, across all hemorrhaged groups). At 90 min after initiation of haemorrhage, resuscitation was performed with 20 ml/kg Ringer's Lactate i.v. over a period of 10 min and then half the shed blood mixed with 100 u/ml heparinised saline i.v. over a period of 50 min At the end of 1 h resuscitation, an i.v. infusion of Ringer's Lactate (1.5 ml/kg/h) was started as fluid replacement and maintained for a further 3 h.

1.3 Quantification of Organ Injury/Dysfunction

Four hours after the onset of resuscitation, 1.2 ml blood was collected from the right carotid artery and decanted into serum gel tubes (Sarstedt, Numbrecht, Germany), after which the heart was removed to terminate the experiment. The samples were centrifuged (9900 rpm for 3 min) to separate serum from which urea, creatinine, aspartate aminotransferase (AST), alanine aminotransferase (ALT) and creatinine kinase (CK) were measured within 24 hours (Idexx Laboratories Ltd., West Yorkshire, UK).

Urine collected during the last 3 h of the experiment was analysed for creatinine levels in order to estimate creatinine clearance as an indicator of glomerular dysfunction and was calculated as follows:

$$\text{Creatinine Clearance (ml/min)} = \frac{\text{urine creatinine (}\mu\text{mol/l)} \times \text{urine flow (ml/min)}}{\text{serum creatinine (}\mu\text{mol/l)}}$$

1.4 Experimental Design

Rats were randomly allocated into the following groups:
(i) Sham (n=4)
(ii) HS Control (n=10)
(iii) HS+Artesunate 1 mg/kg (n=6)
(iv) HS+Artesunate 3 mg/kg (n=7)
(v) HS+Artesunate 10 mg/kg (n=8)

Sham-operated rats underwent identical surgical procedures but without haemorrhage or resuscitation. Animals received either 10% DMSO (1 ml/kg i.v.) or artesunate (1, 3 or 10 mg/kg i.v.) on resuscitation.

1.5 Materials

Unless otherwise stated, all compounds were obtained from Sigma-Aldrich Company Ltd (Poole, Dorset, U.K.). All stock solutions were prepared in non-pyrogenic saline [0.9% (w/v) NaCl: Baxter Healthcare Ltd., Thetford, Norfolk, U.K.]. Ringer's Lactate was also obtained from Baxter Healthcare Ltd. Sodium thiopentone (Thiovet©) was obtained from Link Pharmaceuticals, Horsham, U.K. Multiparin (Heparin injection B.P., 5,000 iu/ml) was obtained from National Veterinary Services, Stoke-on-Trent, U.K., 0.1 ml Multiparin added to 4.9 ml 0.9% (w/v) sodium chloride to give concentration of 100 u/ml and 5 ml Multiparin added to 1 liter 0.9% (w/v) sodium chloride to give concentration of 25 u/ml. Artesunate was also obtained from Sigma-Aldrich Company Ltd (Poole, Dorset, U.K.).

1.6 Statistical Analysis

Each data point represents biochemical measurements obtained from up to 10 separate animals. Data without repeated measurements was assessed by one-way ANOVA followed by Dunnett's post hoc test. Data with repeated measurements was assessed by two-way ANOVA followed by Bonferroni's post hoc test.

1.7 Effect of Artesunate on the Circulatory Failure Caused by Hemorrhagic Shock

Figure 1:
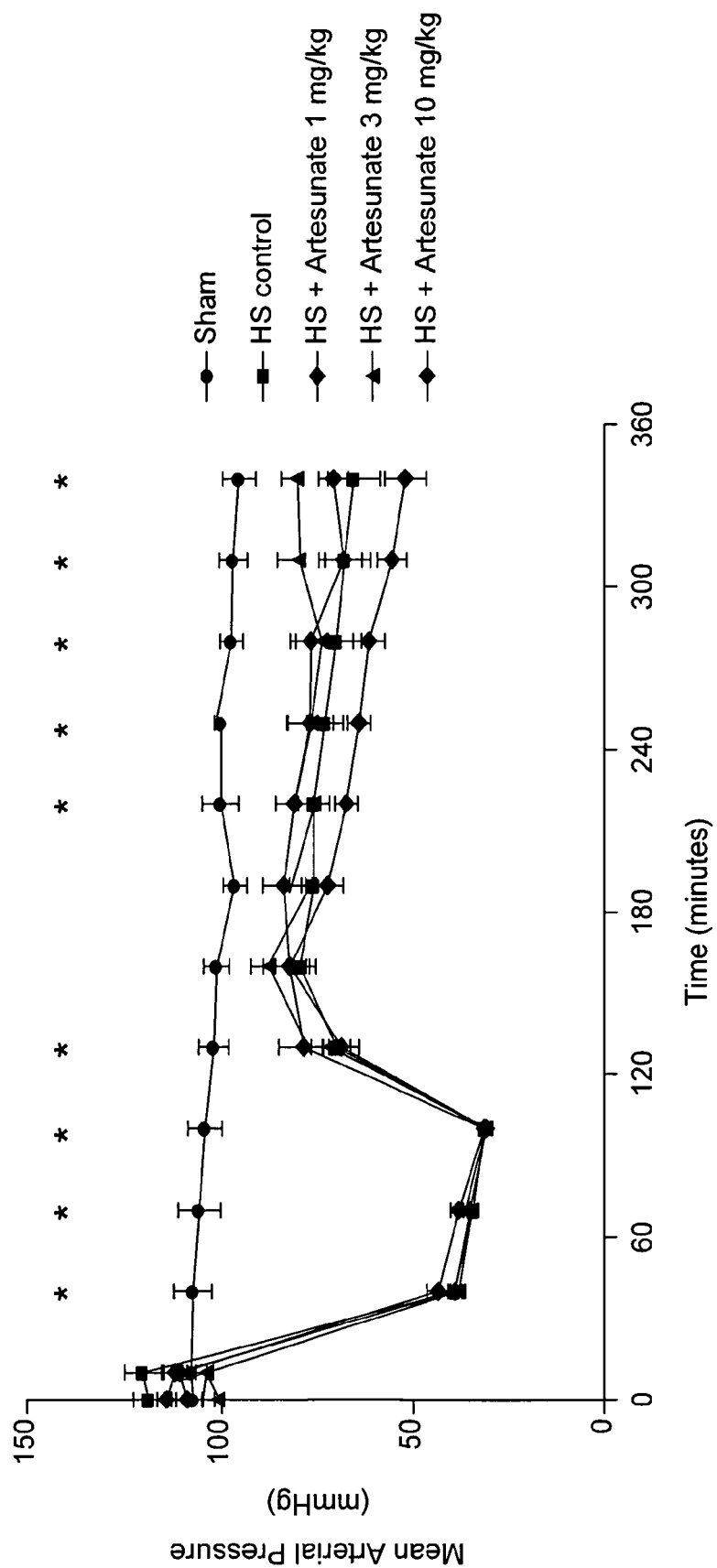

When compared to sham-operated rats, HS-rats treated with vehicle demonstrated a significant reduction in MAP during the resuscitation period ($P<0.05$, FIG. 1). The administration of artesunate (1, 3 or 10 mg/kg) on resuscitation failed to attenuate the decline in MAP caused by haemorrhage during the resuscitation phase ($P>0.05$, FIG. 1).

Figure 2:
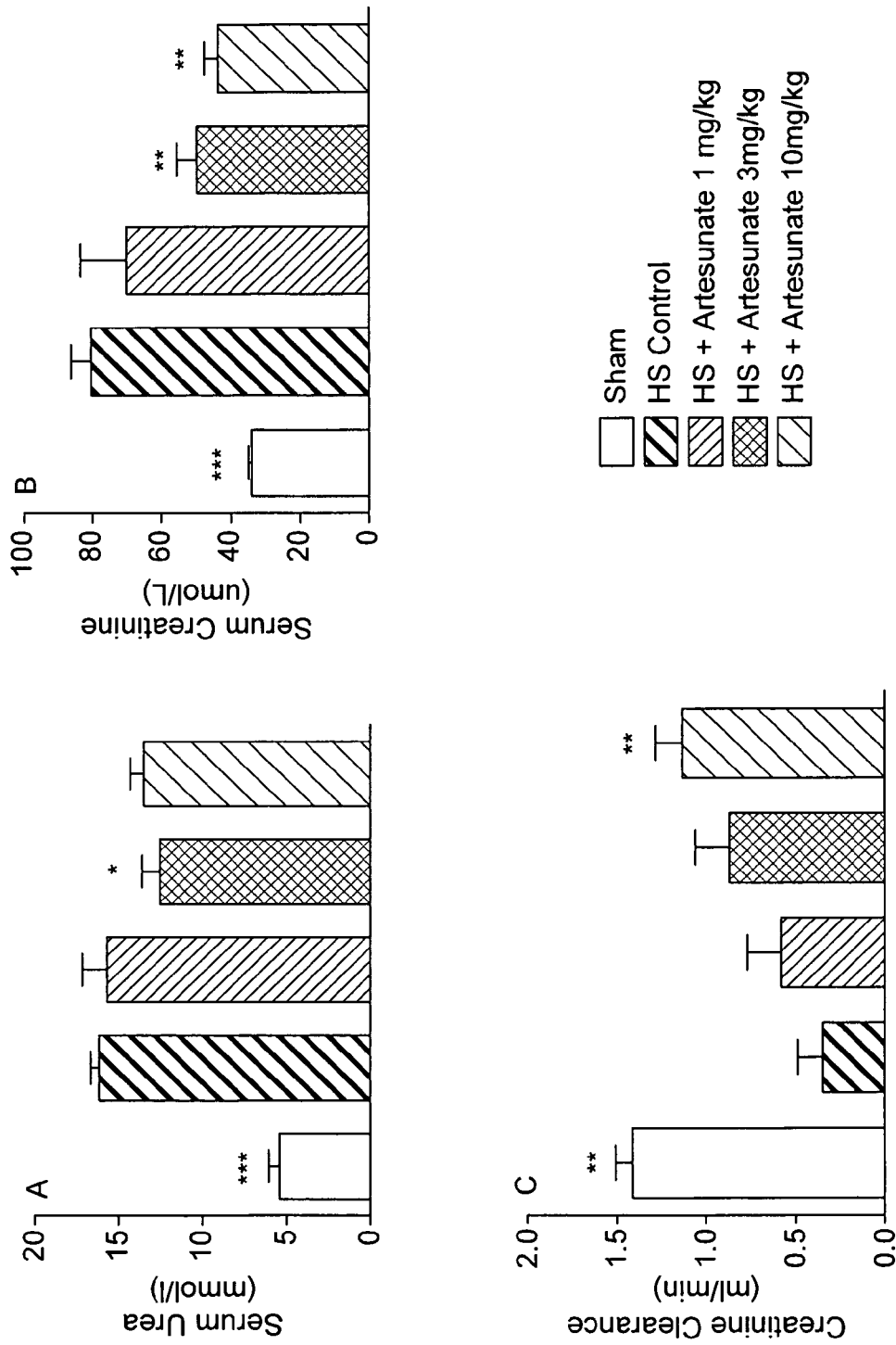

1.8 Effect of Artesunate on the Organ Injury and Dysfunction Induced by Hemorrhagic Shock When compared to sham-operated rats, HS-rats treated with vehicle developed significant increases in serum urea ($P<0.001$, FIG. 2A) and creatinine ($P<0.001$, FIG. 2B); creatinine clearance was significantly reduced when compared to sham-operated rats ($P<0.005$, FIG. 2C) indicating the development of renal and glomerular dysfunction. Treatment of HS-rats with 3 mg/kg artesunate significantly attenuated the rises in serum urea ($P<0.05$, FIG. 2A) and creatinine ($P<0.005$, FIG. 2B) when compared to HS-rats; whereas treatment with 10 mg/kg artesunate significantly attenuated the rise in serum creatinine ($P<0.005$, FIG. 2B) and the fall in creatinine clearance ($P<0.005$, FIG. 2C). Treatment of HS-rats with 1 mg/kg artesunate had no significant effect on the rises in serum urea ($P>0.05$, FIG. 2A) and creatinine ($P>0.05$, FIG. 2B) or on the fall in creatinine clearance ($P>0.05$, FIG. 2C).

Figure 3:
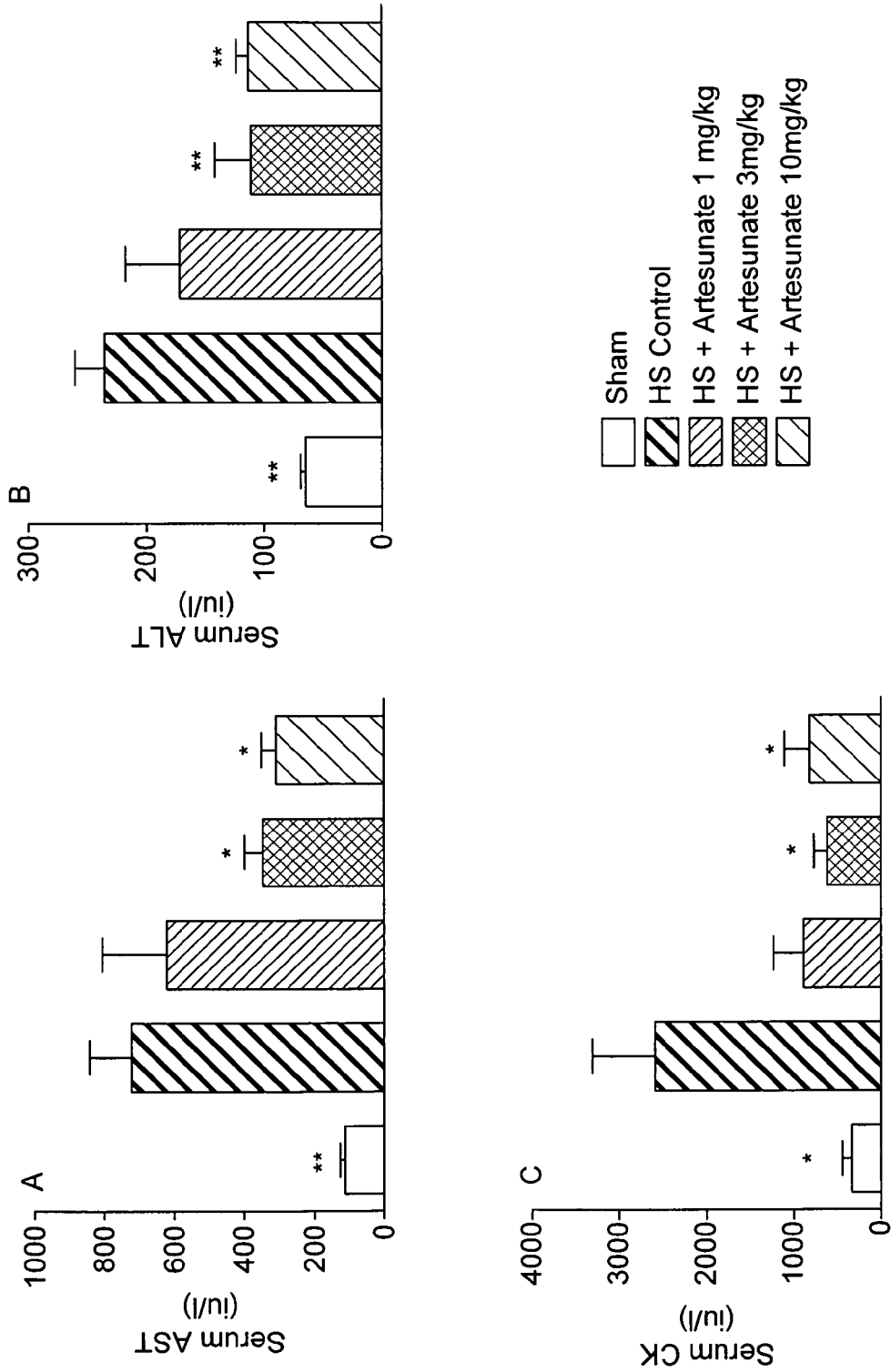

When compared to sham-operated rats, HS-rats treated with vehicle developed significant increases in serum AST ($P<0.005$, FIG. 3A), ALT ($P<0.005$, FIG. 3B) and creatinine kinase ($P<0.05$, FIG. 3C) indicating the development of liver injury and skeletal-muscle injury. Treatment of HS-rats with artesunate (both 3 and 10 mg/kg) significantly attenuated the rises in serum AST ($P<0.05$, FIG. 3A), ALT ($P<0.005$, FIG. 3B) and creatinine kinase ($P<0.05$, FIG. 3C). Treatment with 1 mg/kg artesunate had no significant effect on the rises in serum AST ($P>0.05$, FIG. 3A), ALT ($P>0.05$, FIG. 3B) or creatinine kinase ($P>0.05$, FIG. 3C).

2. Evaluation of the Effects of Artesunate on the Organ Injury and Dysfunction Induced by Burn Injury in the Rat 2.1 Surgical Procedure Twenty-two male Wistar rats (Harlan, Udine, Italy) weighing 300 to 350 g were anaesthetised with sodium pentobarbital (Eutasil™, 60 mg/kg i.p.; Sanofi Veterinária, Algës, Portugal), which was supplemented as required. Anaesthetised rats were shaved (dorsum and abdomen) and placed onto a thermostatically controlled heating mat (Harvard Apparatus Ltd, Kent, U.K.) and body temperature maintained at 37±1° C. by means of a rectal probe attached to a homeothermic blanket. A tracheotomy was performed to maintain airway patency and to facilitate spontaneous respiration. Thirty minutes prior to burn injury, rats were treated with vehicle or drug, as described in section 3.2. To induce burn injury, a 60% third degree skin burn was induced by immersing dorsal shaved skin in 99° C. water for 10 s using a synthetic foam template. The rats were then dried and placed over the heating mat. Rats were sacrificed at 6 hours after burn injury by overdose of the anaesthetic and serum samples obtained for analysis of organ injury and dysfunction.

2.2 Experimental Design

Rats were randomly allocated into the following groups:
(i) Sham (n=4)
(ii) Burn+10% DMSO (n=10)
(iii) Burn+Artesunate (n=9)

Sham-operated rats underwent identical surgical procedures but without burn injury (immersed in room temperature water). Animals received either 10% DMSO (1 ml/kg i.v.) or artesunate (3 mg/kg i.v.) 30 min prior to burn injury and 30 min after burn injury 2.3 Materials Unless otherwise stated, all compounds were obtained from Sigma-Aldrich Quimica S. A. (Sintra, Portugal). Pentobarbital sodium (Eutasil™) was obtained from Sanofi Veterinária (Miraflores, Algés, Portugal). All stock solutions were prepared in non-pyrogenic saline (0.9% NaCl; B. Braun Medical Lda, Queluz, Portugal).

2.4 Statistical Analysis

Each data point represents measurements obtained from up to 10 separate animals. Data was assessed using Mann-Whitney U test.

2.5 Effect of Artesunate on the Renal Dysfunction Induced by Burn Injury

Figure 4:
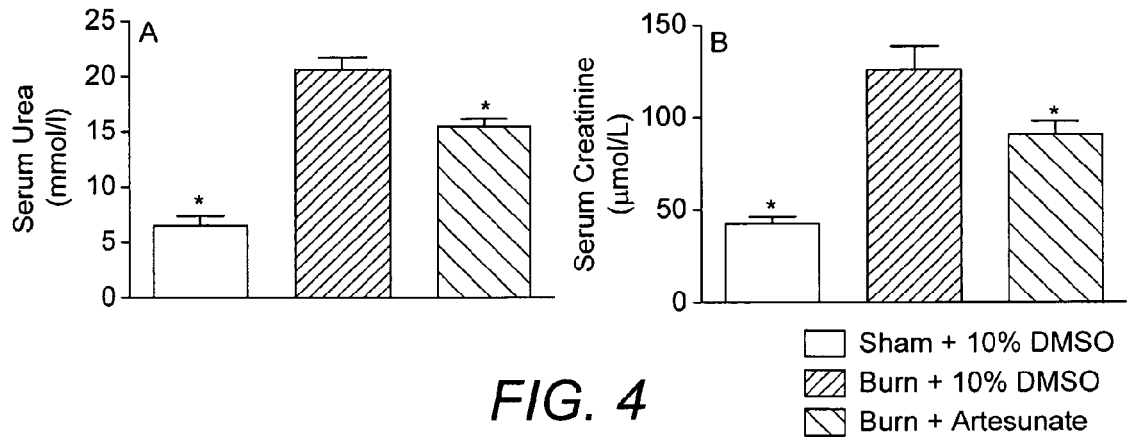
FIG. 4 shows alterations in serum levels of (a) urea and (b) creatinine, in rats subjected to (i) surgical procedure alone and treated with vehicle (Sham+10% DMSO, n=4), burn injury and treated with (ii) vehicle (Burn+10% DMSO, n=10) or (iii) artesunate (Burn+Artesunate, n=9). Data is expressed as mean±SEM, *$P<0.05$ when compared to Burn+10% DMSO.

When compared to sham-operated rats, rats subjected to burn injury and treated with vehicle developed significant increases in serum urea ($P<0.05$, FIG. 4A) and creatinine ($P<0.05$, FIG. 4B) indicating the development of renal dysfunction. Treatment of burn injury rats with 3 mg/kg artesunate significantly attenuated the rises in serum urea ($P<0.05$, FIG. 4A) and creatinine ($P<0.05$, FIG. 4B) when compared to burns injury rats.

2.6 Effect of Artesunate on the Hepatic Injury Induced by Burn Injury

Figure 5:
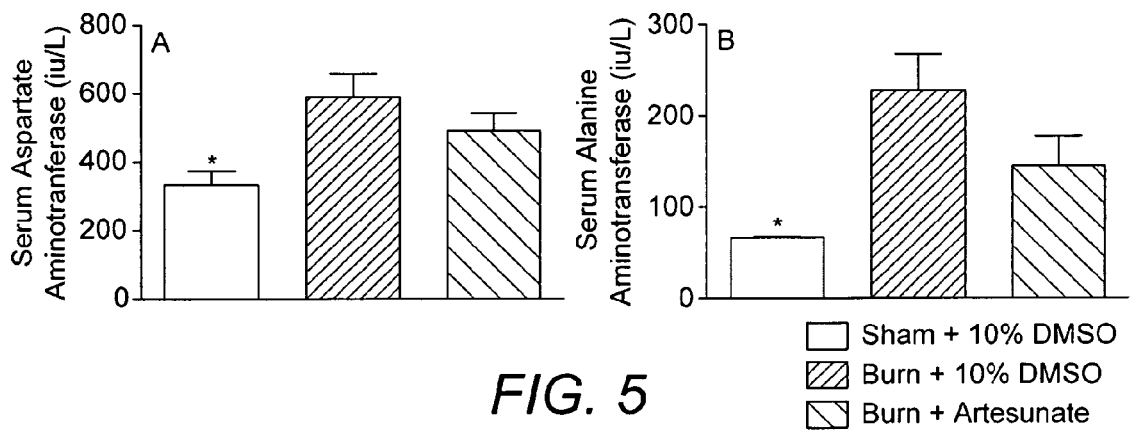
FIG. 5 shows alterations in serum levels of (a) AST and (b) ALT, in rats subjected to (i) surgical procedure alone and treated with vehicle (Sham+10% DMSO, n=4), burn injury and treated with (ii) vehicle (Burn+10% DMSO, n=10) or (iii) artesunate (Burn+Artesunate, n=9). Data is expressed as mean±SEM, *$P<0.05$ when compared to Burn+10% DMSO.

When compared to sham-operated rats, rats subjected to burn injury and treated with vehicle developed significant increases in serum aspartate aminotransferase, AST ($P<0.05$, FIG. 5A) and alanine aminotransferase, ALT ($P<0.05$, FIG. 5B) indicating the development of hepatic injury. Treatment of burn injury rats with 3 mg/kg artesunate had no significant effect on the rises in serum AST ($P>0.05$, FIG. 5A) and ALT ($P>0.05$, FIG. 5B) induced by burn injury.

2.7 Summary

Treatment of rats subjected burn injury with vehicle resulted in significant renal dysfunction (as indicated by rises in serum urea and creatinine) and significant hepatic injury (as indicated by rises in serum AST and ALT).

Treatment of rats subjected to burn injury with 3 mg/kg artesunate resulted in a significant reduction in the renal dysfunction (measured using serum urea and creatinine) caused by burn injury. However, treatment of rats subjected to burn injury with 3 mg/kg artesunate had no significant effect on the hepatic injury (measured using serum AST and ALT) caused by burn injury.

3. Evaluation of the Effects of Artesunate on Infarct Size in a Rat Model of Cerebral Ischaemia and Reperfusion 3.1. Surgical Procedure All procedures were performed in accordance with Italian regulations on the protection of animals used for experimental and other scientific purposes (D.M. 116/92) as well as with the Guide for the Care and Use of Laboratory Animals as adopted and promulgated by the U.S. National Institutes of Health. The experimental protocol was approved by the Turin University Ethics Committee.

Eighteen male Wistar rats (Harlan-Italy; Udine, Italy) weighing 210 to 230 g were anaesthetised with Zoletil 100 (30 mg/kg i.p., mixture of tiletamine and zolazepam, Laboratoires Virbac, France), which was supplemented as needed. The animals were placed onto a thermostatically controlled heating mat (Harvard Apparatus Ltd., Kent, UK) and body temperature was maintained at 37±1° C. by means of a rectal probe attached to a homeothermic blanket. Both common carotid arteries were exposed over a midline incision and a dissection was made between the sternocleidomastoid and the sternohyoid muscles, parallel to the trachea. Each carotid artery was freed from its adventitial sheath and vagus nerve, which was carefully separated and maintained. Ischaemia was achieved by clamping the bilateral common carotid arteries for 30 min using non-traumatic artery clamps (Micro Bulldog Clamps, Harvard Apparatus Ltd., Kent, U.K.). During ischaemia, the animals were monitored for body temperature, respiration pattern, loss of righting reflex, unresponsiveness, corneal reflexes, and fixed and dilated pupils. Recirculation of blood flow was established by releasing the clips and restoration of blood flow in the carotid arteries was confirmed by careful observation. Reperfusion was allowed for 24 h. Post-surgery, the animals were kept for at least 3 h in a 37° C. incubator to ensure that postoperative recovery was satisfactory. Thereafter, they were group-housed under temperature- and light-controlled conditions with food and water ad libitum. At the end of the reperfusion, the anaesthetised rats were killed by decapitation after aortic exsanguination and the forebrain was rapidly dissected at 0° C. The whole hippocampus from both hemispheres was removed and transferred to an appropriate ice-chilled homogenising medium for biochemical assays.

3.2 Determination of Infarct Volume

At the end of reperfusion, the rats were killed with an overdose of Zoletil 100 (mixture of tiletamine and zolazepam) and decapitated. The rats' brains were immediately removed and placed in ice-cold saline for 5 min. Each brain was then placed in a brain matrix and coronal sections were cut into 2-mm slices. Brain slices were immediately immersed in 2% 2,3,5-triphenyltetrazolium chloride monohydrate (TTC) solution (in saline) at 37° C. for 30 min, followed by 4% paraformaldehyde solution. The infarct area and hemisphere area of each section were traced and quantitated by an image analysis system (Inquiry; Loats, Westminster, Md., U.S.A.) and expressed as the percentage infarct area of the whole brain.

3.3 Experimental Design

Rats were randomly allocated into the following groups:
(iv) Sham (n=4)
(v) I/R (n=7)
(vi) I/R+Artesunate 3 mg/kg (n=7)

Sham-operated rats underwent identical surgical procedures but without carotid artery occlusion. Animals received either 30% Hydroxypropyl-beta cyclodextrin (HP-β-CD) (1 ml/kg i.v.) or artesunate (3 mg/kg i.v.) on reperfusion and again 6 h after the onset of reperfusion.

3.4 Materials

Unless otherwise stated, all compounds were obtained from Sigma-Aldrich Company Ltd (Poole, Dorset, U.K.). All stock solutions were prepared in non-pyrogenic saline [0.9% (w/v) NaCl: Baxter Healthcare Ltd., Thetford, Norfolk, U.K.]. The anaesthetic Zoletil 100 (mixture of tiletamine and zolazepam) was obtained from Laboratoires Virbac, Carros Cedex, France.

3.5 Statistical Analysis

Each data point represents measurements from up to 7 separate animals. Data was assessed by one-way ANOVA followed by Dunnett's post hoc test.

3.6 Effect of Artesunate on Cerebral Infarction

When compared to sham-operated rats, rats subjected to cerebral ischaemia and reperfusion resulted in an infarct volume of 27.1±3.9%; administration of artesunate (3 mg/kg) in rats subjected to cerebral ischaemia and reperfusion induced a significant reduction in infarct volume to 19.3±4.3% ($P<0.05$, FIG. 6).

3.7 Summary

Treatment of rats subjected to cerebral ischaemia and reperfusion with vehicle caused the development of an infarct, when compared to sham-operated rats. Treatment of rats subjected to cerebral ischaemia and reperfusion with artesunate (3 mg/kg) significantly reduced the infarct size when compared to rats treated with vehicle.

The results in Examples 1 to 3 demonstrate that artesunate and derivatives thereof could be useful in the treatment of trauma haemorrhage and related conditions, such as trauma haemorrhage-induced organ injury (including acute lung injury and ARDS) or multiple organ failure, or in the treatment of trauma haemorrhage, trauma haemorrhage-induced organ injury, trauma haemorrhage-induced multiple organ failure, stroke or burns injury.

4. Evaluation of the Effects of Artesunate on the Organ Injury and Dysfunction in a Mouse Model of Septic Shock 4.1. Induction of Sepsis Twenty-six male C57BL/6 mice (Harlan Laboratories, Wyton, UK), weighing 20-30 g were used for this experiment. At time point 0 (t=0 h) mice received either LPS (9 mg/kg in 5 ml/kg 0.9% NaCl) or vehicle (5 ml/kg 0.9% NaCl) intraperitoneally (i.p.). Mice were then sacrificed 16-18 h after the injection of LPS by induction of anaesthesia with ketamine (100 mg/ml)/xylazine (20 mg/ml) solution in a 2:1 ratio and removal of the heart.

4.2. Quantification of Organ Injury/Dysfunction

At the end of the experiment, 0.7 ml blood was collected from the right carotid artery and decanted into serum gel tubes (Sarstedt, Numbrecht, Germany). The samples were centrifuged (9900 rpm for 3 min) to separate serum from which urea, creatinine and alanine aminotransferase (ALT) were measured within 24 hours (Idexx Laboratories Ltd., West Yorkshire, UK).

4.3. Experimental Design

Rats were randomly allocated into the following groups:
(vii) Sham (n=5)
(viii) LPS (n=10)
(ix) LPS+Artesunate 10 mg/kg i.p. 1 h post-LPS (n=6)
(x) LPS+Artesunate 10 mg/kg i.v. 1 h post-LPS (n=3)
(xi) LPS+Artesunate 10 mg/kg i.p. 30 min pre-LPS (n=2)

Sham-operated mice received saline (5 ml/kg i.p.) instead of LPS. Mice received either 10% DMSO (5 ml/kg i.p. or i.v.) or artesunate (10 mg/kg i.p. or i.v.) at the time-points described above.

4.4. Materials

Unless otherwise stated, all compounds were obtained from Sigma-Aldrich Company Ltd (Poole, Dorset, U.K.).

All stock solutions were prepared in non-pyrogenic saline [0.9% (w/v) NaCl: Baxter Healthcare Ltd., Thetford, Norfolk, U.K.]. Artesunate was also obtained from Sigma-Aldrich Company Ltd (Poole, Dorset, U.K.).

4.5. Statistical Analysis

Each data point represents biochemical measurements obtained from up to 11 separate animals. Data was assessed using one-factorial ANOVA followed by Dunnett's post-test.

4.6. Effect of Artesunate on the Organ Injury and Dysfunction Induced by Septic Shock When compared to sham-operated mice, mice injected with LPS treated with vehicle developed significant increases in serum urea ($P<0.05$, FIG. 7A), creatinine ($P<0.05$, FIG. 7B) and ALT ($P<0.05$, FIG. 7C) indicating renal dysfunction and hepatic injury. Treatment of septic rats with 10 mg/kg artesunate in all three treatment groups had no significant effect on rises in serum urea ($P>0.05$, FIG. 7A), creatinine ($P>0.05$, FIG. 7B) and ALT ($P<0.05$, FIG. 7C) when compared to septic rats treated with vehicle.

4.7 Summary

Treatment of mice subjected septic shock with vehicle resulted in significant renal dysfunction (as indicated by rises in serum urea and creatinine) and significant hepatic injury (as indicated by a rise in serum ALT). Treatment of rats subjected to septic shock with 10 mg/kg artesunate (in all three treatment groups) had no significant effect on the renal dysfunction (measured using serum urea and creatinine) and hepatic injury (measured using serum ALT) caused by septic shock.

5. Effect of Artesunate Dissolved in 10% DMSO on Myocardial Infarction

This study was carried out on 40 male Wistar rats (Charles River, UK) weighing 240-300 g, receiving a standard diet and water ad libitum.

5.1 Surgical Procedure

Rats were anesthetised with thiopentone sodium (Intraval® 120 mg/kg i.p.). Anesthesia was maintained by supplementary injections of thiopentone sodium as required. The trachea was cannulated and the animals were ventilated with a Harvard ventilator (inspiratory oxygen concentration: 30%; 70 strokes/min, tidal volume: 8-10 ml/kg). Body temperature was maintained at 37±1° C. with the aid of a rectal probe thermometer attached to a homeothermic blanket unit (Harvard Apparatus Ltd., Edenbridge, Kent. U.K.). The right carotid artery was cannulated with a polyethylene catheter and connected to a pressure transducer (Senso-Nor 844, Senso-Nor, Horten, Norway) in order to monitor mean arterial pressure (MAP) and heart rate (HR), which were displayed on a data acquisition system (MacLab 8e, ADI Instruments, Hastings, UK) installed on an IBM compatible computer. The right jugular vein was then cannulated for the administration of drugs and saline. A para-sternal thoracotomy was then performed, using an Electrosurgery device to cauterize the intercostals arteries before cutting through three ribs. The chest was retracted and pericardium dissected from the heart. The left anterior descending (LAD) coronary artery was isolated and a snare occluder was placed around the LAD. The retractor was then removed and the animal was allowed to stabilise for 15 min.

5.2 Ischemia and Reperfusion

The occluder was tightened at time 0. After 25 min of LAD-occlusion, the occluder was released to allow reperfusion of the previously ischemic myocardium (2 h). Hemodynamic parameters were continuously monitored. Baseline readings were taken prior to treatment, and, myocardial IRI. The pressure rate index (PRI), a relative indicator of myocardial oxygen consumption was calculated as a product of the MAP (mmHg) and HR (beats/minute-bpm) and expressed in mm Hg bpm×10-3.

5.3 Quantification of Myocardial Tissue Injury

At the end of the 2 h reperfusion period, the LAD was re-occluded and 1 ml of Evans Blue dye (2% w/v) was injected into the animal, via the jugular vein. The Evans Blue dye stains the tissue it can circulate through, therefore the non-perfused vascular (occluded) tissue remains uncoloured. Each animal was killed with an over-dose of anaesthetic, the heart excised, and excess dye washed off. The heart was then sectioned into slices of 3-4 mm, the right ventricle wall was removed, and the area at risk (AAR—the non-perfused and, hence, non-stained myocardium) was separated from the non-ischemic (blue) tissue. The ischaemic and non-ischaemic tissue was weighed, and the AAR expressed as a percentage of the left ventricle. The tissue from the AAR was cut into small pieces and incubated with p-nitroblue tetrazolium (NBT, 0.5 mg/ml) for 30 min at 37° C. NBT is a reducing agent that reacts with dehydrogenases present in viable (non-infarcted) tissue to produce a dark blue formazan [14]. Infarcted tissue (non-viable) will not have dehydrogenase activity and will therefore fail to stain. The stained tissue was separated from the infarcted tissue, weighed, and the infarct size expressed as a percentage of the AAR.

5.4 Western Blot Analysis

Briefly, heart samples were homogenized at 10% (w/v) in a Potter Elvehjem homogenizer (Wheaton, Millville, N.J., USA) using a homogenisation buffer containing 20 mM HEPES, pH 7.9, 1 mM MgCl2, 0.5 mM EDTA, 1% NP-40, 1 mM EGTA, 1 mM dithiothreitol (DTT), 0.5 mM Phenylmethyl Sulphonyl Fluoride (PMSF), 5 µg/ml aprotinin, 2.5 µg/ml leupeptin. Homogenates were centrifuged at 4,000 g for 5 min at 4° C. Supernatants were removed and centrifuged at 15,000 g at 4° C. for 40 min to obtain the cytosolic fraction. The cytosolic protein contents were determined using a bicinchoninic acid (BCA) Protein Assay kit following the manufacturer's directions. Samples were stored at −80° C. until use. Sixty µg of total protein was loaded. Proteins were separated by 8% sodium dodecyl sulphate-polyacrylamide gel electrophoresis and transferred to a polyvinyldenedifluoride membrane, which was then incubated with SuperBlock blocking buffer. Membranes were incubated with primary antibody (rabbit anti-total GSK-3β, goat anti-pGSK-3β Ser9, rabbit anti-total Akt, rat anti-pAkt Ser473, rabbit anti-eNOS). Blots were then incubated with secondary antibody conjugated with horseradish peroxidase for 30 min at room temperature and developed with the enhanced chemiluminescence detection system. The immunoreactive bands were visualised by autoradiography and the density of the bands were evaluated densitometrically using the Gel Pro® Analyser 4.5, 2000 software (Media Cybernetics, Silver Spring, USA). The membranes were stripped and incubated with β-actin monoclonal antibody for 30 min and subsequently with anti-mouse antibody for 30 min, at room temperature, in order to assess gel-loading homogeneity. Relative band intensity was assessed and normalised against parallel β-actin expression. Each group was then adjusted against corresponding Sham-Control data to establish relative protein expression when compared to Sham-Control animals.

5.5 Statistical Analysis

Hemodynamic parameters were analysed via a two-way analysis of variance (ANOVA) followed by a Bonferroni post-test. Data without repeated measurements were analysed by one-way ANOVA, followed by a Dunnett's post hoc test for multiple comparisons.

5.6 Effect of Regional MI and Artesunate on Haemodynamic Parameters

The baseline values of mean arterial blood pressure in all groups of animals ranged from 105.1±5.6 to 120.2±2.9 mmHg, and were not significantly different between groups (P>0.05, data not shown). Regional myocardial ischaemia followed by reperfusion caused a progressive decline in mean arterial blood pressure to 90.9±5.7 mmHg at the end of the experiment. Pre-treatment of animals with 2 cycles of IPC (5 min) before occlusion of the LAD did not attenuate the fall in mean arterial blood pressure caused by myocardial ischaemia and reperfusion. Bolus treatment of animals with Artesunate (10 mg/kg, 3 mg/kg, 1 mg/kg dissolved in 10% DMSO) upon reperfusion did not attenuate the fall in mean arterial blood pressure caused by myocardial ischaemia and reperfusion (P>0.05 vs. Control).

Baseline values of heart rates in all groups of rats ranged from 393.6±10.5 to 442.7±5.3 beats per minute (bpm), and were not significantly different between groups (P>0.05, data not shown). Pre-treatment of animals with 2 cycles of IPC (5 min) before occlusion of the LAD did not have a significant effect on the heart rate of rats subjected to regional myocardial ischaemia and reperfusion. Bolus treatment of animals with Artesunate (10 mg/kg, 3 mg/kg, 1 mg/kg dissolved in 10% DMSO) upon reperfusion did not have a significant effect on the heart rate of rats subjected to regional myocardial ischaemia and reperfusion (P>0.05 vs. Control).

The pressure rate index, a relative indicator of myocardial oxygen consumption, was calculated as the product of mean arterial blood pressure and heart rate. Baseline values of pressure rate indices in all groups of animals ranged from 41.4±2.6 to 53.2±1.1 beats mmHg min$^{-1}$ 10$^{-3}$ and were not significantly different between groups (P>0.05, data not shown). In rats subjected to myocardial ischaemia and reperfusion, there was a progressive fall in the pressure rate index from 46.0±2.4 to 38.2±3.0 beats mmHg min-1 10-3 at the end of the experiment. Pre-treatment of animals with 2 cycles of IPC (5 min) before occlusion of the LAD did not have a significant effect on the decline in the pressure rate index of rats subjected to regional myocardial ischaemia and reperfusion. Bolus treatment of animals with Artesunate (10 mg/kg, 3 mg/kg, 1 mg/kg dissolved in 10% DMSO) upon reperfusion did not have a significant effect on the decline in the pressure rate index of rats subjected to regional myocardial ischaemia and reperfusion (P>0.05 vs. Control).

5.7 Effect on Area at Risk and Infarct Size

The area at risk of infarction was similar in all groups studied and ranged from 47.0±2.1 to 54.7±2.0% of the left ventricle (P>0.05, FIG. 8A). Sham-operated animals demonstrated an infarct size of 6.2±2.0% of AAR (FIG. 8B). When compared to sham-operated animals, animals subjected to regional myocardial ischaemia (for 25 min) followed by reperfusion (for 2 h) resulted in an infarct size of 59.8±3.2% of the AAR (FIG. 8B). Pre-treatment of animals with 2 cycles of IPC (5 min) before occlusion of the LAD significantly attenuated the infarct size from 59.8±3.2 to 30.3±3.2% (P<0.05, FIG. 8B).

Bolus treatment of animals with Artesunate (10 mg/kg) upon reperfusion significantly attenuated the infarct size from 59.8±3.2 to 42.8±1.7% (Infarct size reduction of 28%, P<0.05, FIG. 8B), when compared to animals subjected to regional myocardial I/R. Treatment with Artesunate (3 mg/kg) upon reperfusion significantly attenuated the infarct size from 59.8±3.2 to 46.9±2.3% (Infarct size reduction of 13%, P<0.05, FIG. 8B), when compared to animals subjected to regional myocardial I/R. In addition, treatment with Artesunate (1 mg/kg) upon reperfusion significantly attenuated the infarct size from 59.8±3.2 to 48.0±3.5% (Infarct size reduction of 12%, P<0.05, FIG. 8B), when compared to animals subjected to regional myocardial I/R.

6. Evaluation of the Effects of Artesunate on Infarct Size in a Rat Model of Regional Myocardial Ischaemia and Reperfusion 6.1. Surgical Procedure This study was carried out on 28 male Wistar rats (Charles River, UK) weighing 240-320 g, receiving a standard diet and water ad libitum.

Rats were anaesthetised with thiopentone sodium (Intraval® 120 mg/kg i.p.). Anaesthesia was maintained by supplementary injections of thiopentone sodium as required. The trachea was cannulated and the animals were ventilated with a Harvard ventilator (inspiratory oxygen concentration: 30%; 70 strokes/min, tidal volume: 8-10 ml/kg). Body temperature was maintained at 37±1° C. with the aid of a rectal probe thermometer attached to a homeothermic blanket unit (Harvard Apparatus Ltd., Edenbridge, Kent. U.K.). The right carotid artery was cannulated with a polyethylene catheter and connected to a pressure transducer (Senso-Nor 844, Senso-Nor, Horten, Norway) in order to monitor mean arterial pressure (MAP) and heart rate (HR), which were displayed on a data acquisition system (MacLab 8e, ADI Instruments, Hastings, UK) installed on an IBM compatible computer. The right jugular vein was then cannulated for the administration of drugs and saline. A para-sternal thoracotomy was then performed, using an Electrosurgery device to cauterize the intercostals arteries before cutting through three ribs. The chest was retracted and pericardium dissected from the heart. The left anterior descending (LAD) coronary artery was isolated and a snare occluder was placed around the LAD. The retractor was then removed and the animal was allowed to stabilise for 15 min.

6.2. Ischaemia and Reperfusion

The occluder was tightened at time 0. After 25 min of LAD-occlusion, the occluder was released to allow reperfusion of the previously ischemic myocardium (2 h). Haemodynamic parameters were continuously monitored. Baseline readings were taken prior to treatment, and, myocardial ischaemia reperfusion (IR) injury. The pressure rate index (PRI), a relative indicator of myocardial oxygen consumption was calculated as a product of the MAP (mmHg) and HR (beats/minute-bpm) and expressed in mm Hg bpm× 10$^{-3}$.

6.3. Quantification of Myocardial Tissue Injury

At the end of the 2 h reperfusion period, the LAD was re-occluded and 1 ml of Evans Blue dye (2% w/v) was injected into the animal, via the jugular vein. The Evans Blue dye stains the tissue it can circulate through, therefore the non-perfused vascular (occluded) tissue remains uncoloured. Each animal was killed with an over-dose of anaesthetic, the heart excised, and excess dye washed off. The heart was then sectioned into slices of 3-4 mm, the right ventricle wall was removed, and the area at risk (AAR—the non-perfused and, hence, non-stained myocardium) was separated from the non-ischemic (blue) tissue. The ischaemic and non-ischaemic tissue was weighed, and the AAR expressed as a percentage of the left ventricle. The tissue from the AAR was cut into small pieces and incubated with p-nitroblue tetrazolium (NBT, 0.5 mg/ml) for 30 min at 37° C. NBT is a reducing agent that reacts with dehydrogenases present in viable (non-infarcted) tissue to produce a dark blue formazan [14]. Infarcted tissue (non-viable) will not have dehydrogenase activity and will therefore fail to stain.

The stained tissue was separated from the infarcted tissue, weighed, and the infarct size expressed as a percentage of the AAR.

6.4 Experimental Design

Rats were randomly allocated into the following groups:
(i) Sham (n=6)
(ii) Control (n=8)
(iii) Artsunate 0.3 mg/kg (n=5)
(iv) Artesunate 1 mg/kg (n=7)
(v) Artesunate 10 mg/kg (n=2)

Sham-operated rats were subjected to surgical procedure without myocardial ischaemia and reperfusion. Animals received either 5% sodium bicarbonate (1 ml/kg i.v.) or artesunate (0.3, 1 or 10 mg/kg i.v.) on resuscitation.

6.5 Statistical Analysis

Haemodynamic parameters were analysed via a two-way analysis of variance (ANOVA) followed by a Dunnett's Multiple Comparison test. Data without repeated measurements were analysed by one-way ANOVA, followed by a Dunnett's post hoc test for multiple comparisons.

6.6 Effect of Regional MI and Artesunate on Haemodynamic Parameters

Regional myocardial ischaemia followed by reperfusion caused a progressive decline in mean arterial blood pressure at the end of the experiment (data not shown). Bolus treatment of animals with artesunate (0.3, 1 or 10 mg/kg) upon reperfusion did not attenuate the fall in mean arterial blood pressure caused by myocardial ischaemia and reperfusion ($P>0.05$ vs. Control).

Baseline values of heart rates in all groups of rats were not significantly different between groups ($P>0.05$, data not shown). Bolus treatment of animals with artesunate (0.3, 1 or 10 mg/kg) upon reperfusion did not have a significant effect on the heart rate of rats subjected to regional myocardial ischaemia and reperfusion ($P>0.05$ vs. Control).

6.7 Effect on Area at Risk and Infarct Size

The area at risk of infarction was similar in all groups studied and ranged from 47.3±2.6 to 55.5±7.5% of the left ventricle ($P>0.05$, FIG. 9A). Sham-operated animals demonstrated an infarct size of 6.2±2.0% of AAR (FIG. 9B). When compared to sham-operated animals, animals subjected to regional myocardial ischaemia (for 25 min) followed by reperfusion (for 2 h) resulted in an infarct size of 57.6±2.1% of the AAR (FIG. 9B). However, when compared to animals subjected to regional myocardial IR injury, bolus treatment of animals with artesunate upon reperfusion at a dose of 0.3 mg/kg significantly attenuated the infarct size from 57.6±2.1, to 44.0±2.61% (FIG. 9B). When treated with artesunate upon reperfusion at a dose of 1 mg/kg this significantly attenuated the infarct size from 57.6±2.1, to 42.6±1.1% (Infarct size reduction of 40%, $P<0.05$) (FIG. 9B). Treatment with 10 mg/kg artesunate had no significant effect on infarct size ($P>0.05$, FIG. 9B).

6.8 Summary

Treatment of rats subjected to myocardial ischaemia and reperfusion with vehicle resulted in a significant increase in infarct size when compared to sham-operated rats. Treatment with vehicle had no significant effect on haemodynamic parameters or the area at risk when compared to sham-operated rats.

Treatment of rats subjected to myocardial ischaemia and reperfusion with 0.3 mg/kg artesunate resulted in a significant decrease in infarct size when compared to vehicle treated rats. Treatment with 0.3 mg/kg artesunate had no significant effect on haemodynamic parameters or the area at risk when compared to vehicle treated rats. Treatment of rats subjected to myocardial ischaemia and reperfusion with 1 mg/kg artesunate resulted in a significant decrease in infarct size when compared to vehicle treated rats. Treatment with 1 mg/kg artesunate had no significant effect on haemodynamic parameters or the area at risk when compared to vehicle treated rats. Treatment of rats subjected to myocardial ischaemia and reperfusion with 10 mg/kg artesunate had no significant effect on haemodynamic parameters, the area at risk or infarct size when compared to vehicle treated rats.

7. Evaluation of the Effects of Artesunate and its Active Metabolite (Dihydroartemisinin) on Infarct Size in a Rat Model of Regional Myocardial Ischaemia and Reperfusion

7.1 Surgical Procedure

This study was carried out on 27 male Wistar rats (Charles River, UK) weighing 240-320 g, receiving a standard diet and water ad libitum.

Rats were anaesthetised with thiopentone sodium (Intraval® 120 mg/kg i.p.). Anaesthesia was maintained by supplementary injections of thiopentone sodium as required. The trachea was cannulated and the animals were ventilated with a Harvard ventilator (inspiratory oxygen concentration: 30%; 70 strokes/min, tidal volume: 8-10 ml/kg). Body temperature was maintained at 37±1° C. with the aid of a rectal probe thermometer attached to a homeothermic blanket unit (Harvard Apparatus Ltd., Edenbridge, Kent. U.K.). The right carotid artery was cannulated with a polyethylene catheter and connected to a pressure transducer (Senso-Nor 844, Senso-Nor, Horten, Norway) in order to monitor mean arterial pressure (MAP) and heart rate (HR), which were displayed on a data acquisition system (MacLab 8e, ADI Instruments, Hastings, UK) installed on an IBM compatible computer. The right jugular vein was then cannulated for the administration of drugs and saline. A para-sternal thoracotomy was then performed, using an Electrosurgery device to cauterize the intercostals arteries before cutting through three ribs. The chest was retracted and pericardium dissected from the heart. The left anterior descending (LAD) coronary artery was isolated and a snare occluder was placed around the LAD. The retractor was then removed and the animal was allowed to stabilise for 15 min.

7.2 Ischaemia and Reperfusion

The occluder was tightened at time 0. After 25 min of LAD-occlusion, the occluder was released to allow reperfusion of the previously ischemic myocardium (2 h). Haemodynamic parameters were continuously monitored. Baseline readings were taken prior to treatment, and, myocardial ischaemia reperfusion (IR) injury. The pressure rate index (PRI), a relative indicator of myocardial oxygen consumption was calculated as a product of the MAP (mmHg) and HR (beats/minute-bpm) and expressed in mm Hg bpm×10$^{-3}$.

7.3 Quantification of Myocardial Tissue Injury

At the end of the 2 h reperfusion period, the LAD was re-occluded and 1 ml of Evans Blue dye (2% w/v) was injected into the animal, via the jugular vein. The Evans Blue dye stains the tissue it can circulate through, therefore the non-perfused vascular (occluded) tissue remains uncoloured. Each animal was killed with an over-dose of anaesthetic, the heart excised, and excess dye washed off. The heart was then sectioned into slices of 3-4 mm, the right ventricle wall was removed, and the area at risk (AAR—the non-perfused and, hence, non-stained myocardium) was separated from the non-ischemic (blue) tissue. The ischaemic and non-ischaemic tissue was weighed, and the AAR expressed as a percentage of the left ventricle. The tissue from the AAR was cut into small pieces and incubated with p-nitroblue tetrazolium (NBT, 0.5 mg/ml) for 30 min at 37° C. NBT is a reducing agent that reacts with dehydrogenases present in viable (non-infarcted) tissue to produce a dark blue formazan[14]. Infarcted tissue (non-viable) will not have dehydrogenase activity and will therefore fail to stain. The stained tissue was separated from the infarcted tissue, weighed, and the infarct size expressed as a percentage of the AAR.

7.4 Experimental Design

Rats were randomly allocated into the following groups:
(vi) Sham (n=6)
(vii) Control (n=8)
(viii) Artesunate 1 mg/kg (n=7)
(ix) Dihydroartemisinin 0.1 mg/kg (n=6)

Sham-operated rats were subjected to surgical procedure without myocardial ischaemia and reperfusion. Animals received either 10% DMSO (1 ml/kg i.v.), artesunate (1 mg/kg i.v.) or dihydroartemisinin, DHA (0.1 mg/kg i.v.) on resuscitation.

7.5 Statistical Analysis

Carried out as described in section 6.5.

7.6 Effect of Regional MI and Artesunate and Dihydroartemisinin on Haemodynamic Parameters The baseline values of mean arterial blood pressure in all groups of animals ranged from 106.8 to 120.2 mmHg, and were not significantly different between groups ($P>0.05$, data not shown). Regional myocardial ischaemia followed by reperfusion caused a progressive decline in mean arterial blood pressure to 101.8 mmHg at the end of the experiment. Bolus treatment of animals with artesunate (1 mg/kg) upon reperfusion did not attenuate the fall in mean arterial blood pressure caused by myocardial ischaemia and reperfusion ($P>0.05$ vs. Control). In addition bolus treatment of animals with dihydroartemisinin (DHA 0.1 mg/kg) upon reperfusion did not attenuate the fall in mean arterial blood pressure caused by myocardial ischaemia and reperfusion ($P>0.05$ vs. Control).

Baseline values of heart rates in all groups of rats ranged from 407.6 to 448.7 beats per minute (bpm), and were not significantly different between groups ($P>0.05$, data not shown). Bolus treatment of animals with artesunate (1 mg/kg) upon reperfusion did not have a significant effect on the heart rate of rats subjected to regional myocardial ischaemia and reperfusion ($P>0.05$ vs. Control). In addition bolus treatment of animals with dihydroartemisinin (DHA 0.1 mg/kg) upon reperfusion also did not have a significant effect on the heart rate of rats subjected to regional myocardial ischaemia and reperfusion ($P>0.05$ vs. Control).

7.7 Effect on Area at Risk and Infarct Size

The area at risk of infarction was similar in all groups studied and ranged from 46.9±2.3 to 57.6±2.12% of the left ventricle ($P>0.05$, FIG. 10A). Sham-operated animals demonstrated an infarct size of 6.2±2.0% of AAR (FIG. 10B). When compared to sham-operated animals, animals subjected to regional myocardial ischaemia (for 25 min) followed by reperfusion (for 2 h) resulted in an infarct size of 57.6±2.12% of the AAR (FIG. 10B). However, when compared to animals subjected to regional myocardial IR injury, bolus treatment of animals with artesunate upon reperfusion at doses of 1 mg/kg significantly attenuated the infarct size from 59.8±3.2, to 36.0±1.1% (Infarct size reduction of 40%, $P<0.05$) (FIG. 10B). In addition, when compared to animals subjected to regional myocardial IR injury, bolus treatment of animals with dihydroartemisinin (DHA 0.1 mg/kg) significantly attenuated the infarct size from 59.8±3.2, to 46.5±1.3% (Infarct size reduction of 40%, $P<0.05$) (FIG. 10B).

7.8 Summary

Treatment of rats subjected to myocardial ischaemia and reperfusion with vehicle resulted in a significant increase in infarct size when compared to sham-operated rats. Treatment with vehicle had no significant effect on haemodynamic parameters or the area at risk when compared to sham-operated rats. Treatment of rats subjected to myocardial ischaemia and reperfusion with 1 mg/kg artesunate resulted in a significant decrease in infarct size when compared to vehicle treated rats. Also, treatment with 1 mg/kg artesunate had no significant effect on haemodynamic parameters or the area at risk when compared to vehicle treated rats. Treatment of rats subjected to myocardial ischaemia and reperfusion with 0.1 mg/kg dihydroartemisinin resulted in a significant decrease in infarct size when compared to vehicle treated rats. Also, treatment with 0.1 mg/kg dihydroartemisinin had no significant effect on haemodynamic parameters or the area at risk when compared to vehicle treated rats.

The results in Examples 5 to 7 demonstrate that artesunate and derivatives thereof (in particular DHA) could be useful in the treatment of myocardial infarction or coronary heart disease or a disorder associated with myocardial infarction or coronary heart disease.

The invention claimed is:

1. A method of treating trauma haemorrhage comprising administering a compound of Formula I

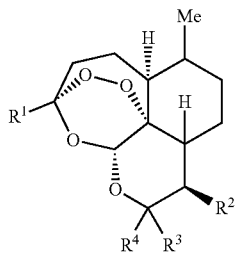

wherein:
- $R^1$ and $R^2$ are independently H or an optionally substituted group selected from an alkyl, a heteroalkyl, an aryl, a heteroaryl, an arylalkyl, and a heteroarylalkyl, and $R^3$ and $R^4$ taken together form a carbonyl (=O); or
- wherein $R^1$ and $R^2$ are independently H or an optionally substituted group selected from an alkyl, a heteroalkyl, an aryl, a heteroaryl, an arylalkyl, and a heteroarylalkyl, $R^3$ is H and $R^4$ is H or —$OR^5$, wherein $R^5$ is H or an optionally substituted group selected from an alkyl, a heteroalkyl, an aryl, a heteroaryl, an arylalkyl, and a heteroarylalkyl;
- or a pharmaceutically acceptable salt or ester thereof, to a patient in need thereof.

2. The method of claim 1, wherein the compound is administered by the oral, parenteral, intravenous, intramuscular, intrathecal or intraperitoneal route, or is administered by inhalation.

3. The method according to claim 1, wherein:
- $R^1$ and $R^2$ are, independently, H or an optionally substituted $C_1$-$C_{10}$ alkyl, and $R^3$ and $R^4$ taken together form a carbonyl (=O) group; or
- $R^1$ and $R^2$ are, independently, H or an optionally substituted $C_1$-$C_{10}$ alkyl, $R^3$ is H, and $R^4$ is H or —$OR^5$, wherein $R^5$ is H or an optionally substituted group selected from an alkyl, a heteroalkyl, an aryl, a heteroaryl, an arylalkyl, and a heteroarylalkyl;
- or a pharmaceutically acceptable salt or ester thereof.

4. The method according to claim 1, wherein:
- $R^1$ and $R^2$ are, independently, H or an optionally substituted $C_1$-$C_3$ alkyl, and $R^3$ and $R^4$ taken together form a carbonyl (=O) group; or
- $R^1$ and $R^2$ are, independently, H or an optionally substituted $C_1$-$C_3$ alkyl, $R^3$ is H and $R^4$ is H or —$OR^5$, wherein $R^5$ is H or an optionally substituted group selected from an alkyl, a heteroalkyl, an aryl, a heteroaryl, an arylalkyl, and a heteroarylalkyl;
- or a pharmaceutically acceptable salt or ester thereof.

5. The method according to claim 1, wherein:
- $R^1$ and $R^2$ are, independently, H or an optionally substituted methyl, and $R^3$ and $R^4$ taken together form a carbonyl (=O) group; or
- $R^1$ and $R^2$ are, independently, H or an optionally substituted methyl, $R^3$ is H, and $R^4$ is —$OR^5$, wherein $R^5$ is H or an optionally substituted group selected from an alkyl, a heteroalkyl, an aryl, a heteroaryl, an arylalkyl, and a heteroarylalkyl;
- or a pharmaceutically acceptable salt or ester thereof.

6. The method according to claim 1, wherein
- $R^1$ and $R^2$ are methyl, and $R^3$ and $R^4$ taken together form a carbonyl (=O) group; or
- $R^1$ and $R^2$ are methyl, $R^3$ is H and $R^4$ is —$OR^5$, wherein $R^5$ is H or an optionally substituted group selected from an alkyl, a heteroalkyl, an aryl, a heteroaryl, an arylalkyl, and a heteroarylalkyl;
- or a pharmaceutically acceptable salt or ester thereof.

7. The method according to claim 1, wherein $R^5$ is H, an alkyl, or an arylalkyl, wherein the alkyl and arylalkyl are, independently, optionally substituted with one more or more of halo, =O, $COOR^6$, $OR^6$ and $OCOR^6$, wherein $R^6$ is H or a $C_1$-$C_6$ alkyl.

8. The method according to claim 1, wherein $R^5$ is selected from the group consisting of H, —$CH_3$, —$CH_2CH_3$, —$CO(CH_2)_2COOH$, and —$CH_2C_6H_6COOH$.

9. The method according to claim 1, wherein the compound is selected from the group consisting of artesunate, artemisinin, artemether, dihydroartemisinin, artelinic acid, and artemotil.

10. The method according to claim 1, wherein the compound administered to the patient is in a pharmaceutical composition comprising a pharmaceutically acceptable excipient.

11. The method according to claim 1, wherein the compound administered to the patient is in a resuscitation solution comprising one or more volume expanders.

12. The method according to claim 1, wherein the compound administered to the patient is in a unit of blood.

* * * * *

SEQUENCE LISTING

```
<160> NUMBER OF SEQ ID NOS: 1

<210> SEQ ID NO 1
<211> LENGTH: 25
<212> TYPE: PRT
<213> ORGANISM: Artificial Sequence
<220> FEATURE:
<223> OTHER INFORMATION: Annexin A1 analog Ac2-26
<220> FEATURE:
<221> NAME/KEY: MOD_RES
<222> LOCATION: 1
<223> OTHER INFORMATION: N-terminal acyl group

<400> SEQUENCE: 1

Ala Met Val Ser Glu Phe Leu Lys Gln Ala Trp Phe Ile Glu Asn Glu
1               5                   10                  15

Glu Gln Glu Tyr Val Gln Thr Val Lys
            20                  25
```